US010901199B2

United States Patent
Mikami et al.

(10) Patent No.: US 10,901,199 B2
(45) Date of Patent: Jan. 26, 2021

(54) ENDOSCOPE SYSTEM HAVING VARIABLE FOCAL LENGTH LENS THAT SWITCHES BETWEEN TWO OR MORE VALUES

(71) Applicant: Sony Olympus Medical Solutions Inc., Tokyo (JP)

(72) Inventors: Takamasa Mikami, Kanagawa (JP); Yuichi Yamada, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 462 days.

(21) Appl. No.: 15/877,210

(22) Filed: Jan. 22, 2018

(65) Prior Publication Data
US 2018/0267291 A1 Sep. 20, 2018

(30) Foreign Application Priority Data

Mar. 17, 2017 (JP) ................................ 2017-053559

(51) Int. Cl.
| | |
|---|---|
| *G02B 23/24* | (2006.01) |
| *A61B 1/05* | (2006.01) |
| *A61B 1/045* | (2006.01) |
| *A61B 1/00* | (2006.01) |
| *A61B 1/04* | (2006.01) |
| *G02B 3/14* | (2006.01) |
| *H04N 5/235* | (2006.01) |

(52) U.S. Cl.
CPC ...... *G02B 23/2484* (2013.01); *A61B 1/00006* (2013.01); *A61B 1/00009* (2013.01); *A61B 1/0019* (2013.01); *A61B 1/00096* (2013.01); *A61B 1/00163* (2013.01); *A61B 1/00188* (2013.01); *A61B 1/042* (2013.01); *A61B 1/045* (2013.01); *A61B 1/05* (2013.01); *G02B 3/14* (2013.01); *G02B 23/2438* (2013.01); *H04N 5/2356* (2013.01)

(58) Field of Classification Search
None
See application file for complete search history.

(56) References Cited

U.S. PATENT DOCUMENTS

| | | | | |
|---|---|---|---|---|
| 4,855,819 A | * | 8/1989 | Hibino | A61B 1/00105 348/70 |
| 4,875,091 A | * | 10/1989 | Yamada | H04N 9/045 348/269 |
| 5,836,867 A | * | 11/1998 | Speier | A61B 1/00188 600/112 |
| 5,912,764 A | * | 6/1999 | Togino | A61B 1/00163 359/367 |

(Continued)

FOREIGN PATENT DOCUMENTS

JP 2014-228851 12/2014

*Primary Examiner* — John P Leubecker
*Assistant Examiner* — Minqiao Huang
(74) *Attorney, Agent, or Firm* — Xsensus LLP

(57) ABSTRACT

An endoscope system includes: an electric lens capable of changing a focal length by applying a voltage; an imaging unit configured to capture a subject image formed by the electric lens to generate image signals; a focus controller configured to perform control to periodically repeat sequential switching of the focal length of the electric lens between two or more values; and a video signal generator configured to generate a video signal to be provided to a display device from the image signals generated by the imaging unit.

18 Claims, 18 Drawing Sheets

(56) References Cited

U.S. PATENT DOCUMENTS

| | | | |
|---|---|---|---|
| 6,398,724 B1 * | 6/2002 | May | A61B 1/00188 600/112 |
| 6,494,826 B1 * | 12/2002 | Chatenever | A61B 1/00188 600/112 |
| 9,247,124 B2 * | 1/2016 | Kawamura | H04N 5/23212 |
| 2002/0085272 A1 * | 7/2002 | Tomioka | G02B 23/2446 359/362 |
| 2007/0038029 A1 * | 2/2007 | Ota | A61B 1/04 600/167 |
| 2007/0156021 A1 * | 7/2007 | Morse | A61B 1/0019 600/167 |
| 2008/0309835 A1 * | 12/2008 | Kuba | G02F 1/133526 349/1 |
| 2009/0058999 A1 * | 3/2009 | Gono | G01J 3/50 348/71 |
| 2013/0038708 A1 * | 2/2013 | Iwasaki | H04N 5/23245 348/65 |
| 2014/0002626 A1 * | 1/2014 | Yu | A61B 1/24 348/66 |
| 2014/0039257 A1 * | 2/2014 | Higuchi | A61B 1/00006 600/109 |
| 2014/0146140 A1 * | 5/2014 | Shimamoto | H04N 5/23212 348/46 |
| 2014/0146219 A1 * | 5/2014 | Kawamura | H04N 5/2356 348/349 |
| 2015/0109513 A1 * | 4/2015 | Nayar | G02B 27/646 348/349 |
| 2015/0238071 A1 * | 8/2015 | Hua | A61B 1/3132 600/109 |
| 2015/0281592 A1 * | 10/2015 | Sarkar | H04N 5/265 348/239 |
| 2016/0299170 A1 * | 10/2016 | Ito | A61B 1/00177 |
| 2016/0327779 A1 * | 11/2016 | Hillman | G02B 23/04 |
| 2016/0363742 A1 * | 12/2016 | Ohno | G02B 3/14 |

* cited by examiner

ENDOSCOPE SYSTEM HAVING VARIABLE FOCAL LENGTH LENS THAT SWITCHES BETWEEN TWO OR MORE VALUES

CROSS-REFERENCE TO RELATED APPLICATION

The present application claims priority to and incorporates by reference the entire contents of Japanese Patent Application No. 2017-053559 filed in Japan on Mar. 17, 2017.

BACKGROUND

The present disclosure relates to an endoscope system that images a subject and processes an image signal of the subject.

In recent years, in medical devices such as endoscopes, high pixelation of an image pickup device, such as a charge-coupled device (CCD) and a complementary metal-oxide-semiconductor (CMOS), has been promoted. The high pixelation of the image pickup device increases a resolution, but causes the problem that a depth of field decreases. To solve this problem, a technology is known in which a plurality of optical systems having different focal lengths are provided in an insertion unit of an endoscope to be inserted in a subject, and a plurality of images captured by the respective optical systems are combined to extend the depth of field (refer to Laid-open Japanese Patent Application No. 2014-228851).

SUMMARY

In the Laid-open Japanese Patent Application No. 2014-228851 described above, a plurality of optical systems are provided in the insertion unit. This causes the problem that the device increases in size.

An endoscope system according to one aspect of the present disclosure may include: an electric lens capable of changing a focal length by applying a voltage; an imaging unit configured to capture a subject image formed by the electric lens to generate image signals; a focus controller configured to perform control to periodically repeat sequential switching of the focal length of the electric lens between two or more values; and a video signal generator configured to generate a video signal to be provided to a display device from the image signals generated by the imaging unit.

DETAILED DESCRIPTION

Figure 1:
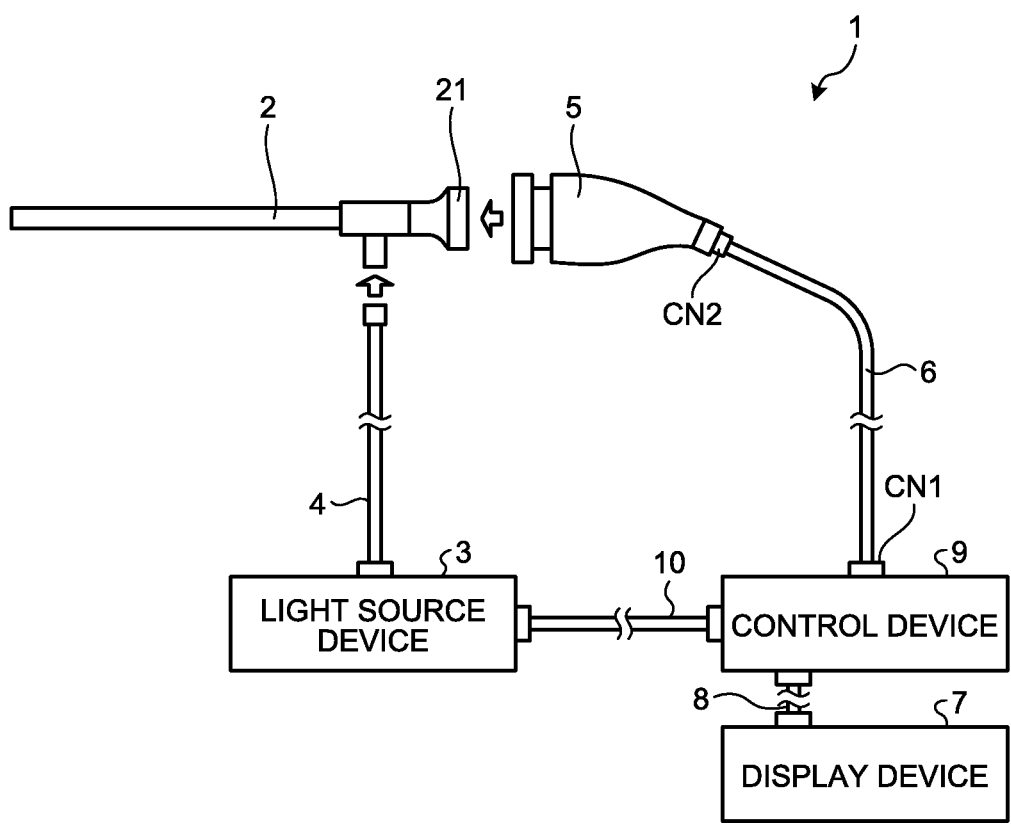
FIG. 1 is a diagram illustrating a schematic configuration of an endoscope system according to a first embodiment.

The following describes details of embodiments for carrying out the present disclosure, with reference to the drawings. The present disclosure is not limited by the embodiments to be described below. The drawings to be referred to in the following description merely schematically illustrate shapes, sizes, and positional relations to the extent of allowing the details to be understood. That is, the present disclosure is not limited to only the shapes, sizes, and positional relations illustrated in the respective drawings. In addition, in the illustration of the drawings, the same parts are assigned with the same reference numerals.

First Embodiment

Schematic Configuration of Endoscope System

FIG. 1 is a diagram illustrating a schematic configuration of an endoscope system according to a first embodiment.

This endoscope system 1 illustrated in FIG. 1 is a device that is used in the medical field, and that captures images in a subject, such as a living body. In the present first embodiment, a description will be given of a rigid endoscope system using a rigid endoscope (insertion unit 2) illustrated in FIG. 1 as the endoscope system 1. The endoscope system 1 is, however, not limited thereto, but may be a flexible endoscope system.

As illustrated in FIG. 1, the endoscope system 1 includes the insertion unit 2, a light source device 3, a light guide 4, an endoscope imaging device 5 (camera head), a first transmission cable 6, a display device 7, a second transmission cable 8, a control device 9, and a third transmission cable 10

The insertion unit 2 is rigid or at least partially flexible, has a long, thin shape, and is inserted into the subject, such as a patient. The insertion unit 2 is provided therein with an optical system that is configured using one or more lenses, and that forms an observed image.

The light source device 3 is connected to one end of the light guide 4, and, under the control of the control device 9, emits (supplies) light for illuminating the inside of the subject to the end of the light guide 4.

One end of the light guide 4 is detachably connected to the light source device 3, and the other end thereof is detachably connected to the insertion unit 2. The light guide 4 transmits the light emitted from the light source device 3 from one end to the other end to supply the light to the insertion unit 2.

An eyepiece 21 of the insertion unit 2 is detachably connected to the endoscope imaging device 5. Under the control of the control device 9, the endoscope imaging device 5 captures the observed image formed by the insertion unit 2, converts the captured image signal (electrical signal) into an optical signal, and outputs the optical signal.

One end of the first transmission cable 6 is detachably connected to the control device 9 through a connector CN1, and the other end thereof is connected to the endoscope imaging device 5 through a connector CN2. The first transmission cable 6 transmits the captured image signal output from the endoscope imaging device 5 to the control device 9, and transmits, for example, control signals, synchronization signals, clocks, and electric power that are output from the control device 9 to the endoscope imaging device 5.

Under the control of the control device 9, the display device 7 displays an observation image based on a video signal processed by the control device 9 and various types of information on the endoscope system 1. The display device 7 is configured using, for example, liquid crystals or organic electro-luminescence (EL). The display device 7 has a monitor size of 31 inches or larger, preferably 55 inches or larger. In the present first embodiment, the display device 7 has a monitor size of 31 inches or larger. The display device 7 is, however, not limited thereto, but may have another monitor size. The monitor size only needs to allow display of, for example, an image having a resolution equal to or more than eight megapixels (such as what is called the 4K resolution of 3840×2160 pixels). As a result, even if an image pickup device (to be described later) provided in the endoscope imaging device 5 is highly pixelated, a high-resolution image may be obtained, and a sense of immersion into the image may be enhanced. Although the high pixelation incurs a problem of small depth of field, the problem may be solved because the depth of field may be virtually extended by performing processing to be described later.

One end of the second transmission cable 8 is detachably connected to the display device 7, and the other end thereof is detachably connected to the control device 9. The second transmission cable 8 transmits the video signal processed by the control device 9 to the display device 7.

The control device 9 is configured including, for example, a central processing unit (CPU), a graphics processing unit (GPU), and various memories, and follows a program recorded in a memory (not illustrated) to integrally control operations of the light source device 3, the endoscope imaging device 5, and the display device 7 through the first transmission cable 6, the second transmission cable 8, and the third transmission cable 10.

One end of the third transmission cable 10 is detachably connected to the light source device 3, and the other end thereof is detachably connected to the control device 9. The third transmission cable 10 transmits control signals from the control device 9 to the light source device 3.

Figure 2:
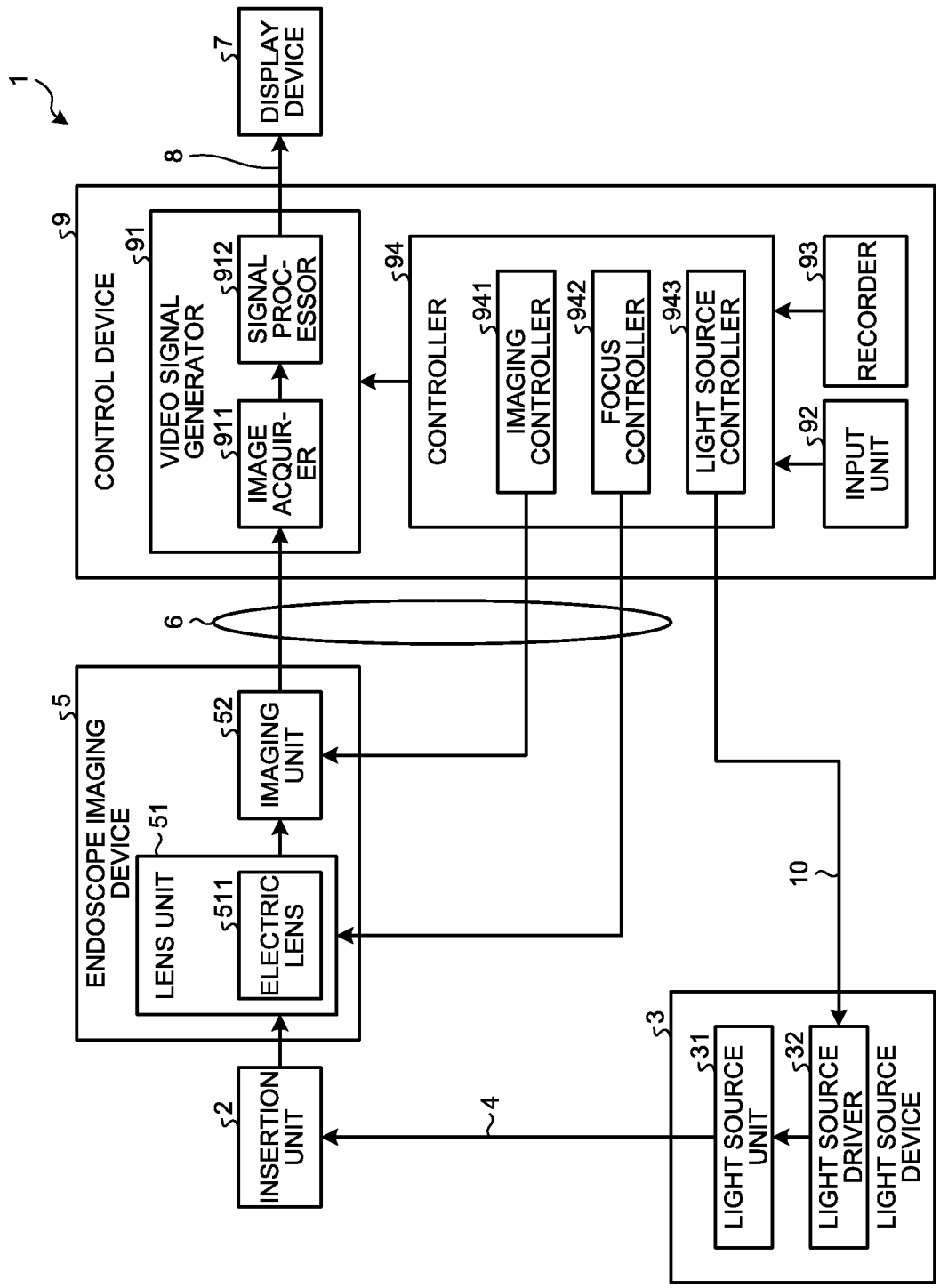
FIG. 2 is a block diagram illustrating functional configurations of a light source device, an endoscope imaging device and a control device included in the endoscope system according to the first embodiment.

The following describes functional configurations of the light source device 3, the endoscope imaging device 5, and the control device 9. FIG. 2 is a block diagram illustrating functional configurations of the light source device 3, the endoscope imaging device 5, and the control device 9 included in the endoscope system 1. For convenience of explanation, FIG. 2 does not illustrate the connectors CN1 and CN2 between each of the endoscope imaging device 5 and the control device 9 and the first transmission cable 6 and connectors between each of the display device 7 and the control device 9 and the second transmission cable 8.

Configuration of Light Source Device

The configuration of the light source device 3 will first be described.

As illustrated in FIG. 2, the light source device 3 includes a light source unit 31 and a light source driver 32. The light source unit 31 is configured using a solid light-emitting element such as a light emitting diode (LED) or a laser diode (LD), a discharge lamp such as a xenon lamp or a metal halide lamp, or a light-emitting member such as a halogen lamp, and, under the drive of the light source driver 32, emits illumination light of white light having a predetermined intensity.

Under the control of the control device 9, the light source driver 32 supplies power to the light source unit 31 so that the light source unit 31 emits the illumination light at the predetermined intensity.

Configuration of Endoscope Imaging Device

The following describes the configuration of the endoscope imaging device 5.

As illustrated in FIG. 2, the endoscope imaging device 5 includes a lens unit 51, and an imaging unit 52.

The lens unit 51 is configured using, for example, an electric lens 511 that is changeable in focal length and focusing by being applied with a voltage, a plurality of optical lenses, and a prism, and forms a subject image focused by the insertion unit 2 on an imaging surface of the imaging unit 52. The lens unit 51 changes the focal length under the control of the control device 9. That is, the lens unit 51 has an optical zooming function of changing an angle of view and a focusing function of changing the focal length, both under the control of the control device 9. In the present first embodiment, the electric lens 511 is configured using a liquid lens.

Figure 3:
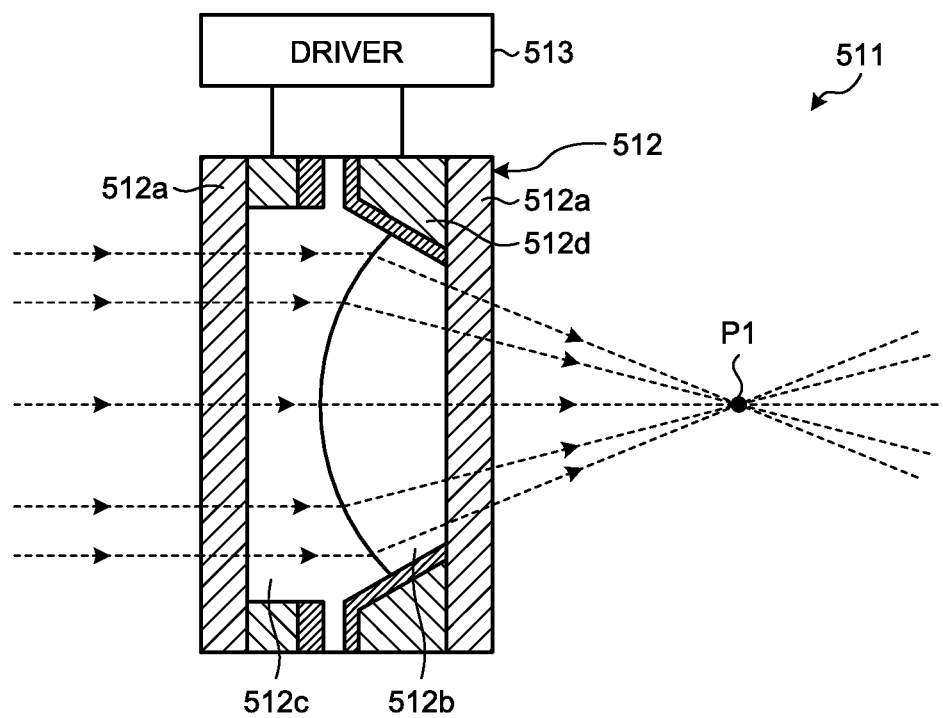
FIG. 3 is a sectional view schematically illustrating a configuration of an electric lens according to the first embodiment.

FIG. 3 is a sectional view schematically illustrating the configuration of the electric lens 511. With reference to FIG. 3, the following describes the case where the electric lens 511 is configured using the liquid lens. The electric lens 511 is, however, not limited to this configuration, but may be configured using, for example, a liquid crystal lens that is changeable in focal length by being applied with a voltage. For convenience of explanation, FIG. 3 illustrates only the main part of the liquid lens.

As illustrated in FIG. 3, the electric lens 511 includes a liquid lens 512 and a driver 513 for driving the liquid lens 512.

The liquid lens 512 is formed of transparent members, and includes hermetically sealed cell 512a, water 512b serving as an immiscible liquid filled in the cell 512a, oil 512c serving as another immiscible liquid filled in the cell 512a, and an application part 512d for applying electrostatic pressure to each of the water 512b and the oil 512c.

Under the control of the control device 9, the driver 513 adjusts the voltage applied to the application part 512d to change a focal position P1 and the focal length of the liquid lens 512.

In the thus configured electric lens 511, the driver 513 applies the voltage, under the control of the control device 9, to the application part 512d to change positions of the water 512b and the oil 512c with the electrostatic pressure so as to change the focal length.

Referring back to FIG. 2, the description of the configuration of the endoscope imaging device 5 will be continued.

The imaging unit 52 is configured using an image pickup device (not illustrated), such as a CCD or a CMOS, that receives the light of the subject image formed by the lens unit 51 and converts the received light into an electrical signal under the control of the control device 9, and a sensor chip (not illustrated) provided by integrating, for example, a signal processor (not illustrated) that applies signal processing (such as an analog-to-digital (A/D) conversion) to the electrical signal (analog signal) from the image pickup device to output a digital image signal. The number of effective pixels of the imaging unit 52 (image pickup device) is equal to or more than eight megapixels (such as what is called the 4K resolution of 3840×2160 pixels). In this case, although the increase in the number of effective pixels of the imaging unit 52 involves the reduction in the depth of field, this problem may be solved because the depth of field may be virtually extended by performing the processing to be described later. In the present first embodiment, the imaging unit 52 transmits the digital image signal to the control device 9 in the form of the electrical signal. The image signal is, however, not limited to this form. For example, the imaging unit 52 may be provided with an electrical-to-optical (E/O) converter, and the image signal may be transmitted to the control device 9 in the form of an optical signal. In the present first embodiment, a light receiving surface of the imaging unit 52 is provided with a primary color filter of the Bayer array (red (R), green (G), and blue (B)). Naturally, the light receiving surface may be configured using a complementary color filter (magenta (Mg), cyan (Cy), and yellow (Ye)), instead of such a color filter.

Configuration of Control Device

The following describes the configuration of the control device 9.

As illustrated in FIG. 2, the control device 9 includes a video signal generator 91, an input unit 92, a recorder 93, and a controller 94.

The video signal generator 91 acquires the image signal from the endoscope imaging device 5 through the first transmission cable 6, applies various types of processing to the acquired image signal to generate the video signal, and outputs the video signal to the display device 7. The video signal generator 91 includes an image acquirer 911 and a signal processor 912.

The image acquirer 911 acquires the image signal from the endoscope imaging device 5 through the first transmission cable 6, and outputs the acquired image signal to the signal processor 912.

The signal processor 912 applies white balance processing, gamma correction processing, and demosaicing processing to the image signal received from the image acquirer 911 to generate video signals (demosaiced images) of respective R, G, and B colors, combines the generated video signals of the respective colors to generate a video signal of a color image, and outputs the generated video signal to the display device 7.

The input unit 92 receives instruction signals for instructing various operations for the endoscope system 1, and outputs the received instruction signals to the controller 94. The input unit 92 is configured using, for example, buttons, a touchscreen, and switches.

The recorder 93 records various programs executed by the endoscope system 1 and information being processed. The recorder 93 is configured using a synchronous dynamic random access memory (SDRAM), a flash memory, or the like.

The controller 94 integrally controls various units of the endoscope system 1. The controller 94 is configured using, for example, a central processing unit (CPU). The controller 94 includes an imaging controller 941, a focus controller 942, and a light source controller 943.

The imaging controller 941 controls the imaging of the imaging unit 52. Specifically, the imaging controller 941 controls the frame rate and the exposure time of the imaging unit 52. The imaging controller 941 may set the frame rate for the imaging unit 52 to generate the image signal to a frame rate higher than a frame rate at which the display device 7 displays an image corresponding to the video signal, and may control the imaging unit 52 to perform imaging at the set frame rate. For example, if the frame rate of the display device 7 is 60 frames per second (fps), the imaging controller 941 may control the imaging unit 52 to perform the imaging at 120 fps (multiple of the frame rate of the display device 7 by an integer equal to or larger than one).

The focus controller 942 controls the focal length of the lens unit 51. Specifically, the focus controller 942 performs control to periodically repeat sequential switching of the focal length of the electric lens 511 between two or more values. For example, the focus controller 942 performs control to periodically repeat alternate switching of the focal length of the electric lens 511 between a long focus side and a short focus side the focal length of which is smaller than that of the long focus side. In addition, the focus controller 942 performs control to switch the focal length of the electric lens 511 for each frame of the video signal generated by the video signal generator 91. Furthermore, the focus controller 942 performs control to switch the focal length of the electric lens 511 during an output period in which the imaging unit 52 outputs the image signal.

The light source controller 943 controls the drive of the light source device 3. Specifically, based on luminance information included in the video signal of the color image, the light source controller 943 controls the intensity of the illumination light emitted by the light source unit 31 of the light source device 3.

Processing by Endoscope System

The following describes processing executed by the endoscope system 1.

Figure 4:
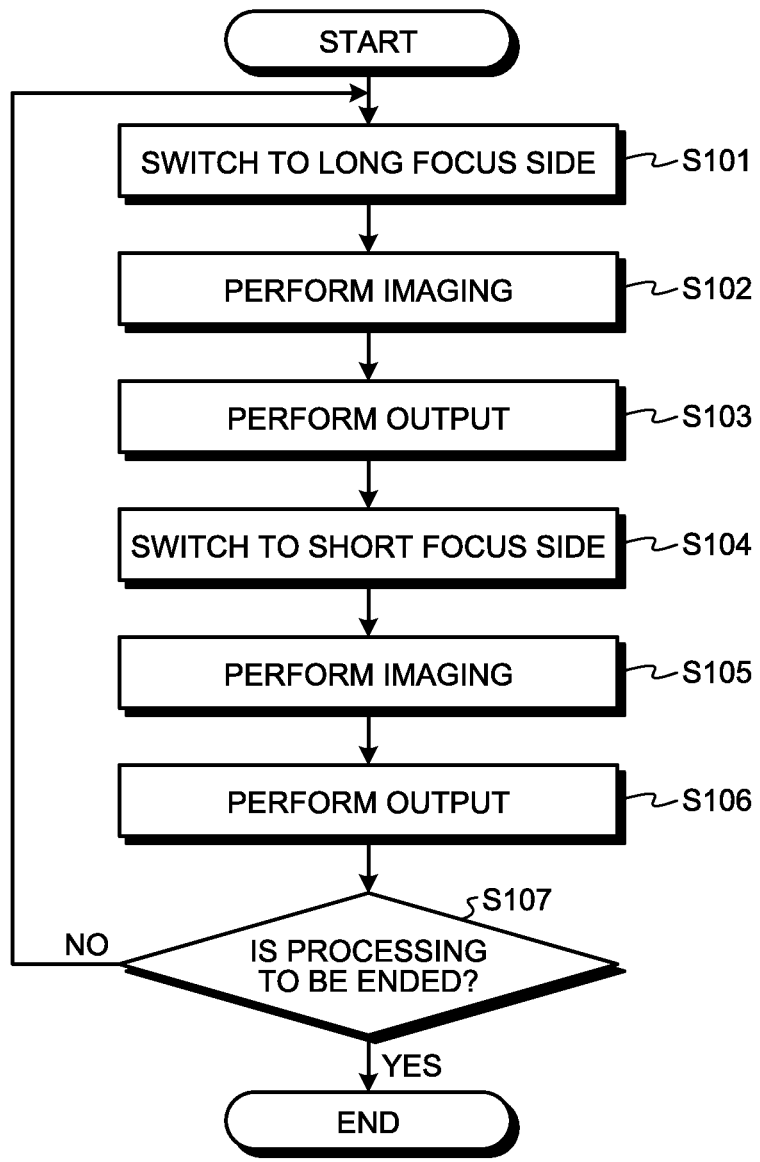
FIG. 4 is a flowchart illustrating an outline of processing executed by the endoscope system according to the first embodiment.

FIG. 4 is a flowchart illustrating the outline of the processing executed by the endoscope system 1. For convenience of description, the following describes the switching of the focal length of the electric lens 511 between the two sides of the long focus side and the short focus side. The switching is, however, not limited thereto. The focus controller 942 may perform control to, for example, repeat sequential switching of the focal length of the electric lens 511 between a plurality of focal lengths set according to operations of the input unit 92.

As illustrated in FIG. 4, the focus controller 942 first switches the focal length of the electric lens 511 to the long focus side (Step S101). In this case, the focus controller 942 performs control to switch the focal length of the electric lens 511 to the long focus side during the output period in which the imaging unit 52 outputs the image signal, or a vertical synchronizing signal and a horizontal synchronizing signal.

Subsequently, the imaging controller 941 controls the imaging unit 52 to execute imaging (Step S102).

Thereafter, the video signal generator 91 outputs the video signal of the color image generated based on the image signal generated by the imaging unit 52 to the display device 7 (Step S103).

Subsequently, the focus controller 942 switches the focal length of the electric lens 511 to the short focus side (Step S104). In this case, the focus controller 942 performs control to switch the focal length of the electric lens 511 to the short focus side during the output period in which the imaging unit 52 outputs the image signal.

Thereafter, the imaging controller 941 controls the imaging unit 52 to execute imaging (Step S105).

Subsequently, the video signal generator 91 outputs the video signal of the color image generated based on the image signal generated by the imaging unit 52 to the display device 7 (Step S106).

Subsequently, if an instruction signal to end the examination of the subject is received through the input unit 92 (Yes at Step S107), the endoscope system 1 ends this process. If, instead, the instruction signal to end the examination of the subject is not received through the input unit 92 (No at Step S107), the endoscope system 1 returns to Step S101 described above.

According to the first embodiment described above, the focus controller 942 performs the control to periodically repeat the sequential switching of the focal length of the electric lens 511 between two or more values, and the video signal generator 91 alternately outputs the video signals generated using the image signals generated by the imaging unit 52 at different focal lengths, to the display device 7. Consequently, the depth of field may be extended without an increase in size.

According to the first embodiment, since the focus controller 942 performs the control to sequentially switch the focal length of the electric lens 511 for each frame of the video signal generated by the video signal generator 91, the display device 7 may display an image with a schematically extended depth of field by quickly and alternately displaying the video signals generated at different focal lengths. As a result, a user is allowed to naturally view the image with the extended depth of field without feeling uncomfortable.

According to the first embodiment, since the focus controller 942 performs the control to switch the focal length of the electric lens 511 during the output period in which the imaging unit 52 outputs the image signal, high-speed imaging may be executed without reducing the frame rate of the imaging unit 52.

According to the first embodiment, since the focus controller 942 performs the control to repeat the alternate switching between the long focus side and the short focus side, the electric lens 511 may be simply controlled.

Second Embodiment

The following describes a second embodiment. In the first embodiment described above, the depth of field is schematically extended by quickly and sequentially displaying the video signals generated at different focal lengths on the display device 7. In the present second embodiment, however, the image with the extended depth of field is generated and displayed on the display device by combining the video signals generated at different focal lengths. The following describes the configuration of an endoscope system according to the present second embodiment, and then describes processing executed by the endoscope system according to the present second embodiment. The same components as those of the endoscope system 1 according to the above-described first embodiment are assigned with the same reference numerals, and the description thereof will not be repeated.

Configuration of Endoscope System

Figure 5:
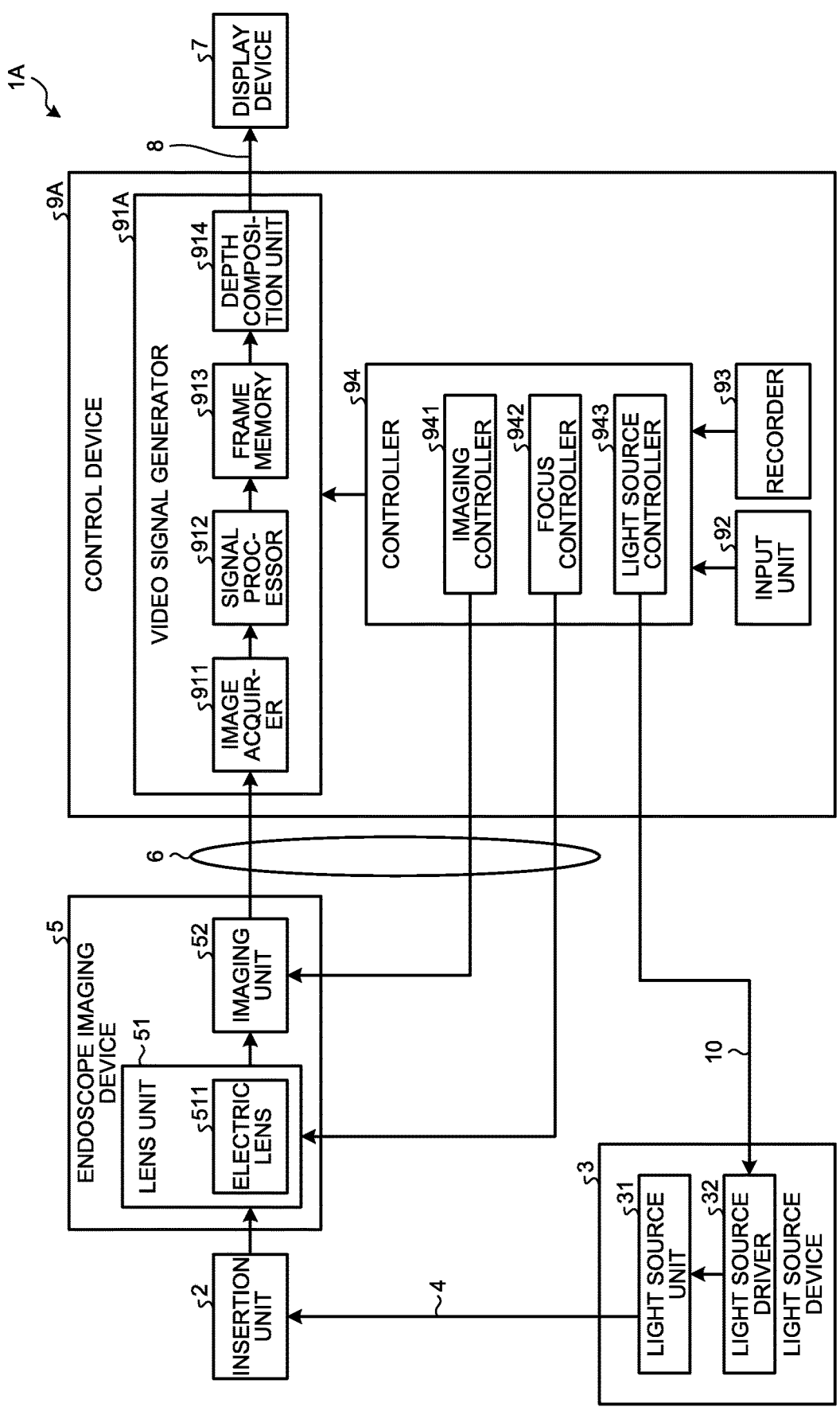
FIG. 5 is a block diagram illustrating functional configurations of the light source device, the endoscope imaging device and a control device included in an endoscope system according to a second embodiment.

FIG. 5 is a block diagram illustrating functional configurations of the light source device, the endoscope imaging device and a control device included in the endoscope system according to the second embodiment.

This endoscope system 1A illustrated in FIG. 5 includes a control device 9A instead of the control device 9 of the endoscope system 1 according to the first embodiment described above.

Configuration of Control Device

The configuration of the control device 9A will be described.

The control device 9A includes a video signal generator 91A instead of the video signal generator 91 according to the first embodiment described above. The video signal generator 91A acquires the image signal from the endoscope imaging device 5 through the first transmission cable 6, applies various types of processing to the acquired image signal to generate the video signal, and outputs the video signal to the display device 7. The video signal generator 91A includes a frame memory 913 and a depth composition unit 914, in addition to the configuration of the video signal generator 91 according to the first embodiment described above.

The frame memory 913 sequentially records the video signal of the color image generated by the signal processor 912 to record a predetermined number of frames of video signals.

The depth composition unit 914 generates a video signal with an extended depth of field based on the video signals generated at different focal lengths and recorded in the frame memory 913, and outputs the generated video signal to the display device 7. For example, the depth composition unit 914 generates the video signal with the extended depth of field based on the video signal of the color image captured by the imaging unit 52 at the long focus side focal length of the electric lens 511 and the video signal of the color image captured by the imaging unit 52 at the short focus side focal length of the electric lens 511, and outputs the generated video signal to the display device 7. Specifically, the depth composition unit 914 compares sharpness (contrast)

between the video signal of the color image captured by the imaging unit 52 at the long focus side focal length of the electric lens 511 and the video signal of the color image captured by the imaging unit 52 at the short focus side focal length of the electric lens 511 for each pixel, and generates the video signal with the extended depth of field using pixel values of pixels having higher sharpness (contrast).

When the depth composition unit 914 generates the video signal with the extended depth of field using the video signals generated by the imaging unit 52 at different focal lengths of the electric lens 511, the depth composition unit 914 may generate the video signal with the extended depth of field (depth composite image) by combining the pixel value of each pixel (each set of pixel coordinates) by obtaining a weighted average using a known technique of Laplacian filter processing so as to increase the weight of a pixel having higher sharpness (contrast) between pixels (pixel coordinates) corresponding to each other among a plurality of pixels. Naturally, the depth composition unit 914 may generate the video signal with the extended depth of field (depth composite image) by using only the pixel values of pixels having the highest sharpness (contrast) among pixels (pixel coordinates) corresponding to each other among a plurality of pixels.

When the depth composition unit 914 generates the video signal with the extended depth of field using the video signals generated at different focal lengths, the depth composition unit 914 may generate the video signal with the extended depth of field (depth composite image) by extracting a region having higher sharpness (contrast) in each of a plurality of images corresponding to the video signals, and by combining the pixel values of the extracted region having higher sharpness (contrast) in each of the images. The depth composition unit 914 is not limited to the depth-of-field composition processing described above, but may use another known technique of the depth-of-field composition processing.

Processing by Endoscope System

The following describes processing executed by the endoscope system 1A.

Figure 6:
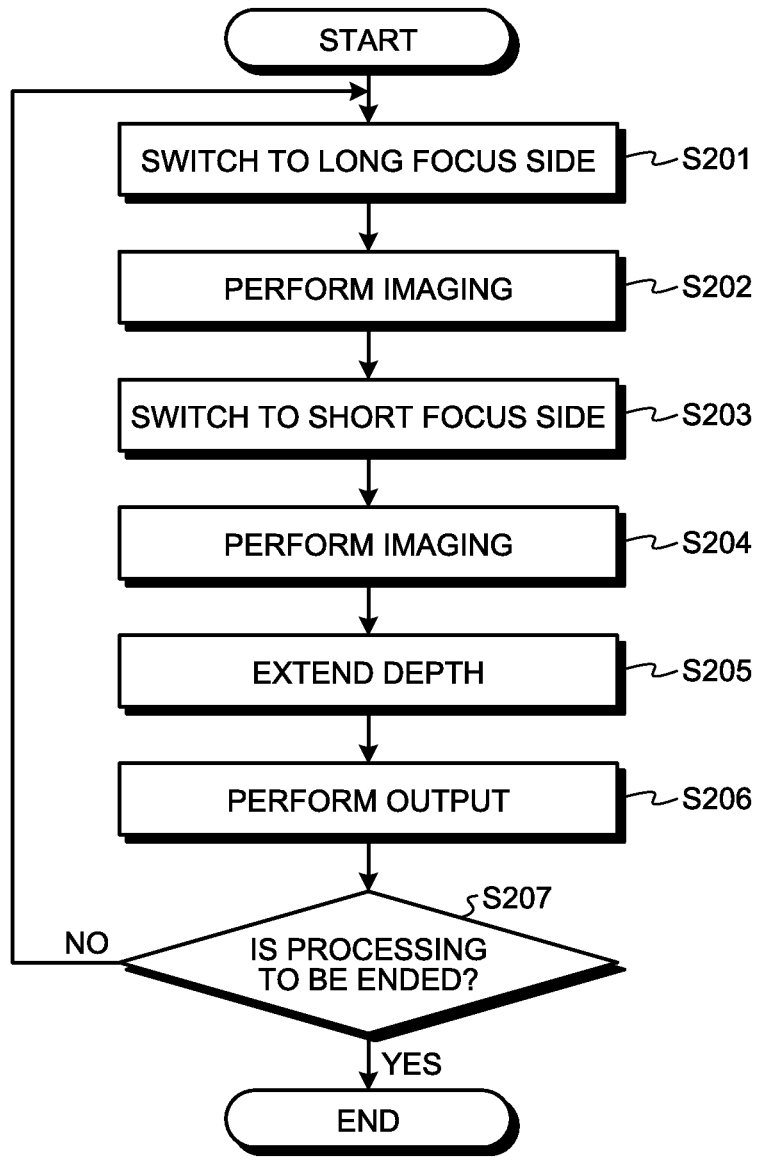
FIG. 6 is a flowchart illustrating an outline of processing executed by the endoscope system according to the second embodiment.

FIG. 6 is a flowchart illustrating the outline of the processing executed by the endoscope system 1A. For convenience of description, the following describes the switching of the focal length of the electric lens 511 between the two sides of the long focus side and the short focus side. The switching is, however, not limited thereto. For example, the focus controller 942 may perform the control to sequentially switch the focal length of the electric lens 511 between a plurality of focal lengths set according to the operations of the input unit 92.

As illustrated in FIG. 6, the focus controller 942 first switches the focal length of the lens unit 51 to the long focus side (Step S201). In this case, the focus controller 942 performs the control to switch the focal length of the electric lens 511 to the long focus side during the output period in which the imaging unit 52 outputs the image signal, or the vertical synchronizing signal and the horizontal synchronizing signal.

Figure 7:
FIG. 7 is a diagram schematically illustrating an exemplary image generated by an imaging unit when the focal length of the electric lens according to the second embodiment is on a long focus side.

Subsequently, the imaging controller 941 controls the imaging unit 52 to execute the imaging (Step S202). In this case, as illustrated in FIG. 7, an image W1 corresponding to the image signal generated by the imaging unit 52 is in focus on the deeper side (rear side), and out of focus on the front side.

Thereafter, the focus controller 942 switches the focal length of the lens unit 51 to the short focus side (Step S203). In this case, the focus controller 942 performs the control to switch the focal length of the electric lens 511 to the short focus side during the output period in which the imaging unit 52 outputs the image signal.

Figure 8:
FIG. 8 is a diagram schematically illustrating an exemplary image generated by the imaging unit when the focal length of the electric lens according to the second embodiment is on a short focus side.

Subsequently, the imaging controller 941 controls the imaging unit 52 to execute the imaging (Step S204). In this case, as illustrated in FIG. 8, an image W2 corresponding to the image signal generated by the imaging unit 52 is in focus on the front side, and out of focus on the deeper side.

Figure 9:
FIG. 9 is a diagram illustrating an exemplary image generated by a depth composition unit according to the second embodiment.

Thereafter, the depth composition unit 914 generates the video signal of the composite image with the extended depth of field based on the video signals on the long focus side and the short focus side generated at different focal lengths and recorded in the frame memory 913 (Step S205), and outputs the video signal of the composite image to the display device 7 (Step S206). Specifically, as illustrated in FIG. 9, the depth composition unit 914 generates the video signal of a composite image W3 with the extended depth of field based on the image W1 on the long focus side generated at Step S202 described above and the image W2 on the short focus side generated at Step S204 described above. In this manner, the image with the extended depth of field of the subject may be obtained.

Subsequently, if the instruction signal to end the examination of the subject is received through the input unit 92 (Yes at Step S207), the endoscope system 1A ends this process. If, instead, the instruction signal to end the examination of the subject is not received through the input unit 92 (No at Step S207), the endoscope system 1A returns to Step S201 described above.

According to the second embodiment described above, since the depth composition unit 914 generates the video signal with the extended depth of field using two or more image signals generated by the imaging unit 52 at different focal lengths, the same effect as that of the above-described first embodiment is obtained, and the depth of field may be extended without an increase in size.

In the second embodiment, the depth composition unit 914 generates the video signal with the extended depth of field using the two temporally earlier and later image signals generated on the long focus side and the short focus side by the imaging unit 52. However, the video signal with the extended depth of field (depth-of-field composite image) may be generated, for example, using any one image signal of a plurality of frames generated at each focal length and recorded in the frame memory 913. In this case, the depth composition unit 914 only needs to generate the video signal with the extended depth of field (depth-of-field composite image) by selecting, from among the frames generated at each focal length, an image signal (image) of the frame having the highest contrast or the highest sharpness for each focal length, and by applying the above-described depth-of-field composition processing to the selected image signal of each of the frames. In this manner, the video signal with an excellent resolution and the extended depth of field may be obtained.

Third Embodiment

The following describes a third embodiment. An endoscope system according to the present third embodiment has the same configuration as that of the endoscope system 1A according to the second embodiment described above, but processing executed by the endoscope system differs therebetween. Specifically, in the second embodiment described above, the imaging controller 941 controls the imaging unit 52 to be exposed for a constant exposure time regardless of the focal length of the electric lens 511. In the present third embodiment, however, the exposure time of the imaging unit is controlled according to the focal length of the electric lens. The following describes the processing executed by the endoscope system according to the present third embodiment. The same components as those of the endoscope system 1A according to the above-described second embodiment are assigned with the same reference numerals, and the description thereof will not be repeated.

Processing by Endoscope System

Figure 10:
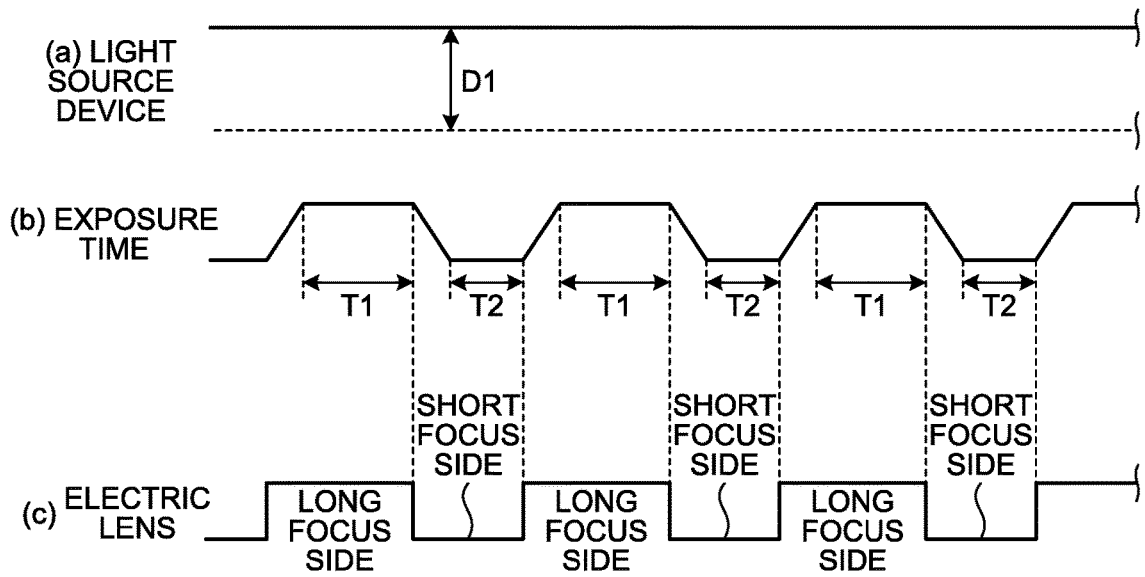
FIG. 10 illustrates a timing diagram of processing executed by an endoscope system according to a third embodiment.

FIG. 10 illustrates a timing diagram of the processing executed by the endoscope system 1 according to the third embodiment. In FIG. 10, Part (a) of FIG. 10 illustrates the intensity of the illumination light emitted by the light source device 3; Part (b) of FIG. 10 illustrates the exposure time of the imaging unit 52; and Part (c) of FIG. 10 illustrates the state of the focal length of the electric lens 511. For convenience of explanation, FIG. 10 illustrates the switching of the focal length of the electric lens 511 between the two sides of the long focus side and the short focus side. The switching is, however, not limited thereto. The focus controller 942 may perform the control to, for example, repeat the sequential switching of the focal length of the electric lens 511 between a plurality of focal lengths set according to the operations of the input unit 92.

As illustrated in FIG. 10, the imaging controller 941 controls the exposure time of the imaging unit 52 such that an exposure time T1 when the focal length of the electric lens 511 is on the long focus side is longer than an exposure time T2 when the focal length of the electric lens 511 is on the short focus side (T1>T2). Specifically, when the electric lens 511 performs imaging at the long focus side focal length, it is difficult for the illumination light emitted by the light source device 3 to reach the deeper side of the subject, so that the light reflected from the subject is weaker. Therefore, the imaging controller 941 increases the exposure time T1 of the imaging unit 52 to prevent insufficiency of light exposure. In contrast, when the electric lens 511 performs imaging at the short focus side focal length, the light reflected from the subject is stronger. Therefore, the imaging controller 941 sets the exposure time T2 of the imaging unit 52 shorter than the exposure time T1 to prevent the light exposure of the imaging unit 52 from exceeding an appropriate value.

According to the third embodiment described above, since the imaging controller 941 controls the imaging unit 52 such that the exposure time T1 of the imaging unit 52 on the long focus side is longer than the exposure time T2 of the imaging unit 52 on the short focus side, the video signal with the extended depth of field may be generated with appropriate light exposure.

In the third embodiment, the imaging controller 941 controls the imaging unit 52 so as to switch the exposure time of the imaging unit 52 on each of the long focus side and the short focus side of the electric lens 511. The control is, however, not limited thereto. The imaging controller 941 may control the imaging unit 52 so as to switch the exposure time of the imaging unit 52 for each focal length to which the electric lens 511 may be switched. Specifically, the imaging controller 941 only needs to control the exposure time of the imaging unit 52 such that the exposure time of the imaging unit 52 increases as the focal length of the electric lens 511 increases.

Modification of Third Embodiment

The following describes a modification of the third embodiment.

Figure 11:
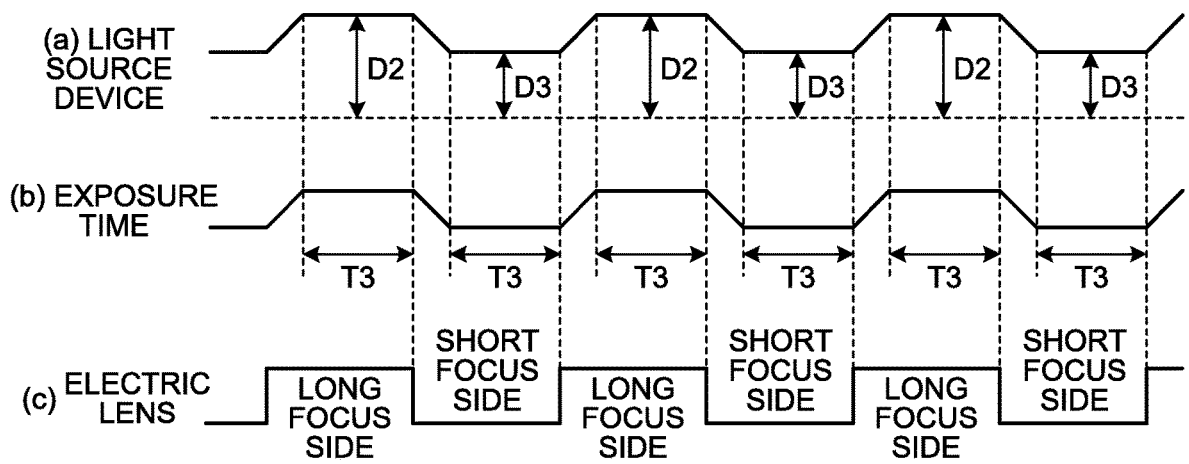
FIG. 11 illustrates a timing diagram of processing executed by an endoscope system according to a modification of the third embodiment.

FIG. 11 illustrates a timing diagram of processing executed by the endoscope system 1 according to the modification of the third embodiment. In FIG. 11, Part (a) of FIG. 11 illustrates the intensity of the illumination light emitted by the light source device 3; Part (b) of FIG. 11 illustrates the exposure time of the imaging unit 52; and Part (c) of FIG. 11 illustrates the state of the focal length of the electric lens 511. For convenience of explanation, FIG. 11 illustrates the switching of the focal length of the electric lens 511 between the two sides of the long focus side and the short focus side. The switching is, however, not limited thereto. The focus controller 942 may perform the control to, for example, repeat the sequential switching of the focal length of the electric lens 511 between a plurality of focal lengths set according to the operations of the input unit 92.

As illustrated in FIG. 11, the imaging controller 941 controls the imaging unit 52 to perform the imaging for a constant exposure time regardless of the focal length of the electric lens 511. In this case, the light source controller 943 performs control to adjust the intensity of the illumination light emitted by the light source device 3 according to the focal length of the electric lens 511. Specifically, the light source controller 943 controls the light source device 3 to emit the illumination light at an intensity D2 when the focal length of the electric lens 511 is on the long focus side, and controls the light source device 3 to emit the illumination light at an intensity D3 when the focal length of the electric lens 511 is on the shorter focus side, the intensity D2 being higher than the intensity D3 (D2>D3). In this manner, the imaging unit 52 may be controlled to perform the imaging with appropriate light exposure without changing the frame rate of the imaging unit 52.

According to the modification of the third embodiment described above, since the light source controller 943 performs the control to adjust the intensity of the illumination light emitted by the light source device 3 according to the focal length of the electric lens 511, the imaging unit 52 may be controlled to perform the imaging with appropriate light exposure without changing the frame rate of the imaging unit 52.

In the modification of the third embodiment, the light source controller 943 controls the light source device 3 such that the intensity D2 of the illumination light on the long focus side is higher than the intensity D3 of the illumination light on the short focus side. The control is, however, not limited thereto. The intensity of the illumination light emitted by the light source device 3 may be adjusted for each focal length to which the electric lens 511 may be switched. Specifically, the light source controller 943 may control the light source device 3 such that the intensity of the illumination light emitted by the light source device 3 increases as the focal length of the electric lens 511 increases.

Fourth Embodiment

The following describes a fourth embodiment. An endoscope system according to the present fourth embodiment has the same configuration as that of the endoscope system 1A according to the second embodiment described above, but processing executed by the endoscope system differs therebetween. Specifically, the present fourth embodiment switches the processing according to a mode corresponding to an instruction signal received from the input unit. The following describes the processing executed by the endoscope system according to the present fourth embodiment. The same components as those of the endoscope system 1A according to the above-described second embodiment are assigned with the same reference numerals, and the description thereof will not be repeated.

Processing by Endoscope System

Figure 12:
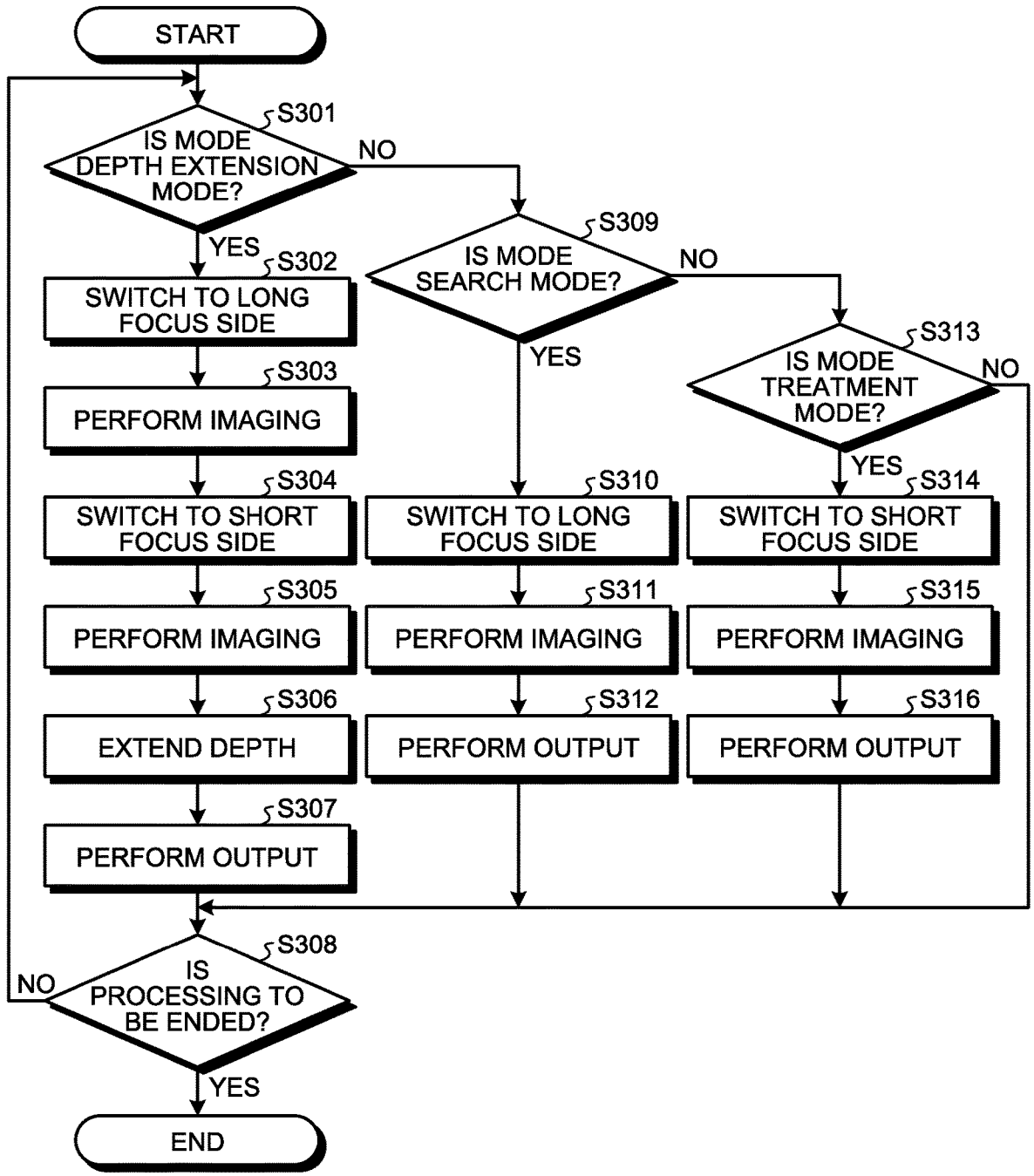
FIG. 12 is a flowchart illustrating an outline of processing executed by an endoscope system according to a fourth embodiment.

FIG. 12 is a flowchart illustrating the outline of the processing executed by the endoscope system 1A according to the fourth embodiment.

As illustrated in FIG. 12, a controller 94 first determines whether the endoscope system 1A has been set, according to an operation of the input unit 92, to a depth extension mode in which the depth of field of the electric lens 511 is extended (Step S301). If the controller 94 determines that the endoscope system 1A has been set to the depth extension mode (Yes at Step S301), the endoscope system 1A goes to Step S302 to be described later.

Steps S302 to S308 respectively correspond to Steps S201 to S207 in FIG. 6 described above.

If, at Step S301, the controller 94 determines that the endoscope system 1A has not been set to the depth extension mode (No at Step S301), the endoscope system 1A goes to Step S309 to be described later.

Subsequently, the controller 94 determines whether the endoscope system 1A has been set, according to an operation of the input unit 92, to a search mode in which a lesion of the subject is searched for (Step S309). If the controller 94 determines that the endoscope system 1A has been set to the search mode (Yes at Step S309), the endoscope system 1A goes to Step S310 to be described later.

Thereafter, the focus controller 942 performs the control to switch the focal length of the electric lens 511 to the long focus side (Step S310).

Subsequently, the imaging controller 941 controls the imaging unit 52 to perform the imaging (Step S311), and the video signal generator 91 applies various types of image processing to the image signal generated by the imaging unit 52 to generate the video signal, and outputs the generated video signal to the display device 7 (Step S312). After Step S312, the endoscope system 1A goes to Step S308.

If, at Step S309, the controller 94 determines that the endoscope system 1A has not been set to the search mode (No at Step S309), the endoscope system 1A goes to Step S313 to be described later.

Subsequently, the controller 94 determines whether the endoscope system 1A has been set, according to an operation of the input unit 92, to a treatment mode in which the subject is treated (Step S313). If the controller 94 determines that the endoscope system 1A has been set to the treatment mode (Yes at Step S313), the endoscope system 1A goes to Step S314 to be described later.

Thereafter, the focus controller 942 performs the control to switch the focal length of the electric lens 511 to the short focus side (Step S314).

Subsequently, the imaging controller 941 controls the imaging unit 52 to perform the imaging (Step S315), and the video signal generator 91 applies the various types of image processing to the image signal generated by the imaging unit 52 to generate the video signal, and outputs the generated video signal to the display device 7 (Step S316). After Step S316, the endoscope system 1A goes to Step S308.

If, at Step S313, the controller 94 determines that the endoscope system 1A has not been set to the treatment mode (No at Step S313), the endoscope system 1A goes to Step S308.

According to the fourth embodiment described above, since the focus controller 942 switches the focal length of the electric lens 511 according to the mode set by the operation of the input unit 92, the subject may be imaged at a focal length according to a request of an operator.

In the fourth embodiment, the focus controller 942 switches the focal length of the electric lens 511 according to the mode set by the operation of the input unit 92. The focal length of the electric lens 511 may, however, be switched, for example, based on the video signal generated by the video signal generator 91A.

Fifth Embodiment

The following describes a fifth embodiment. An endoscope system according to the present fifth embodiment differs from the endoscope system 1A according to the second embodiment described above in configuration and in processing executed. The following describes the configuration of the endoscope system according to the present fifth embodiment, and then describes the processing executed by the endoscope system according to the present fifth embodiment. The same components as those of the endoscope system 1A according to the above-described second embodiment are assigned with the same reference numerals, and the description thereof will not be repeated.

Configuration of Endoscope System

Figure 13:
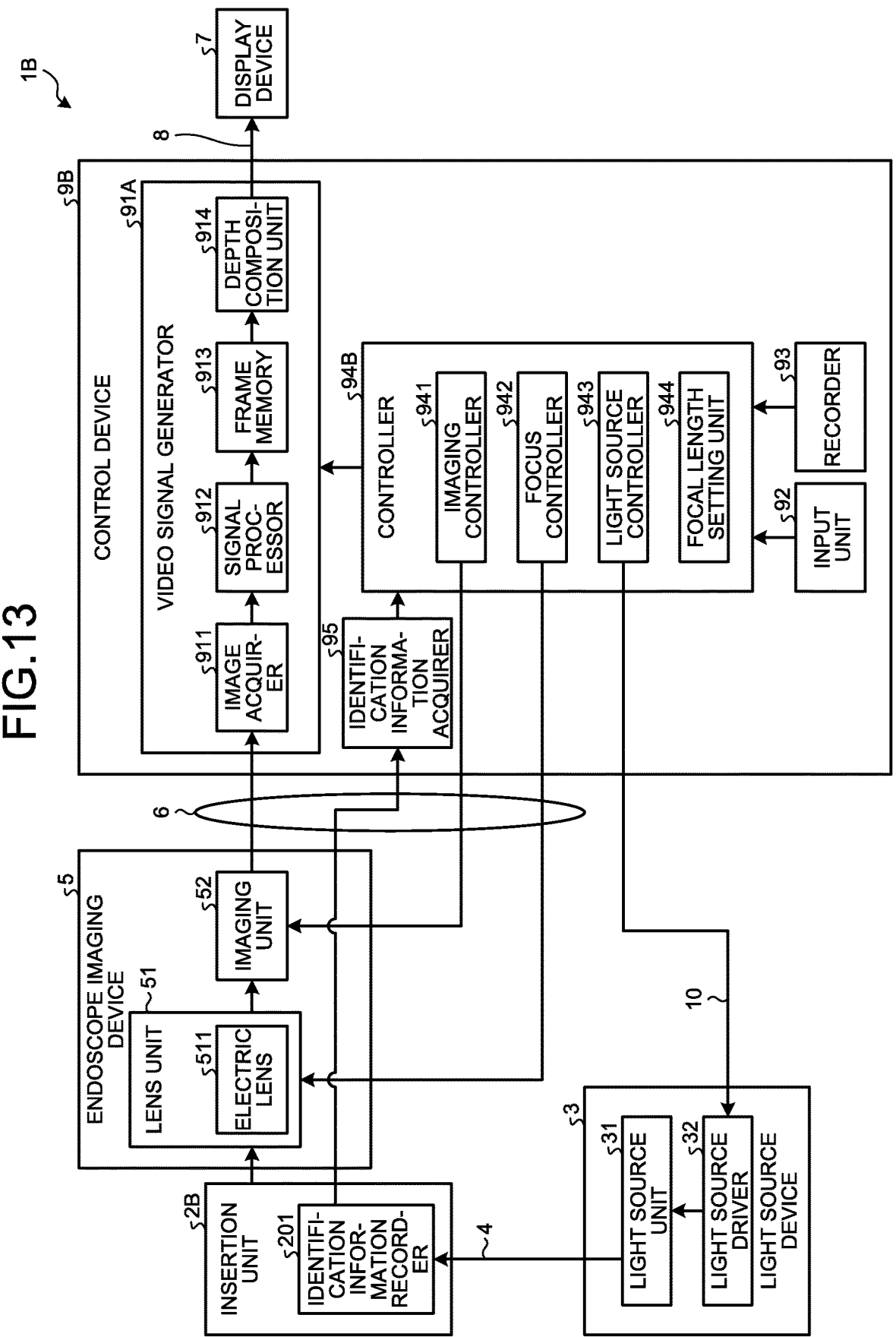
FIG. 13 is a block diagram illustrating functional configurations of an insertion unit, a light source device, an endoscope imaging device and a control device included in an endoscope system according to a fifth embodiment.

FIG. 13 is a block diagram illustrating functional configurations of an insertion unit, a light source device, an endoscope imaging device and a control device included in the endoscope system according to the fifth embodiment.

This endoscope system 1B illustrated in FIG. 13 includes an insertion unit 2B and a control device 9B instead of the insertion unit 2 and the control device 9 of the endoscope system 1A according to the second embodiment described above.

Configuration of Insertion Unit

The configuration of the insertion unit 2B will first be described.

The insertion unit 2B is rigid or at least partially flexible, has a long, thin shape, and is inserted into the subject, such as a patient. The insertion unit 2B is provided therein with an optical system that is configured using one or more lenses, and that forms an observed image. The insertion unit 2B includes an identification information recorder 201 for recording identification information identifying the insertion unit 2B. The identification information includes the magnification, the focal length, the oral insertability, the insertion length, the form, and the type of the insertion unit 2B.

Configuration of Control Device

The following describes the configuration of the control device 9B.

The control device 9B includes a controller 94B instead of the controller 94 of the control device 9A according to the second embodiment described above, and further includes an identification information acquirer 95.

The identification information acquirer 95 acquires the identification information from the identification information recorder 201 of the insertion unit 2B, through the endoscope imaging device 5 and the first transmission cable 6, and outputs the acquired identification information to the controller 94B.

The controller 94B integrally controls various units of the endoscope system 1B. The controller 94B is configured using, for example, a CPU. The controller 94B further includes a focal length setting unit 944, in addition to the configuration of the controller 94 according to the second embodiment described above.

The focal length setting unit 944 sets a plurality of focal lengths of the electric lens 511 based on the identification information acquired by the identification information acquirer 95. For example, the focal length setting unit 944 increases the number of focal lengths set for the electric lens 511 with increase in the focal length included in the identification information acquired by the identification information acquirer 95.

Processing by Endoscope System

The following describes the processing executed by the endoscope system 1B.

Figure 14:
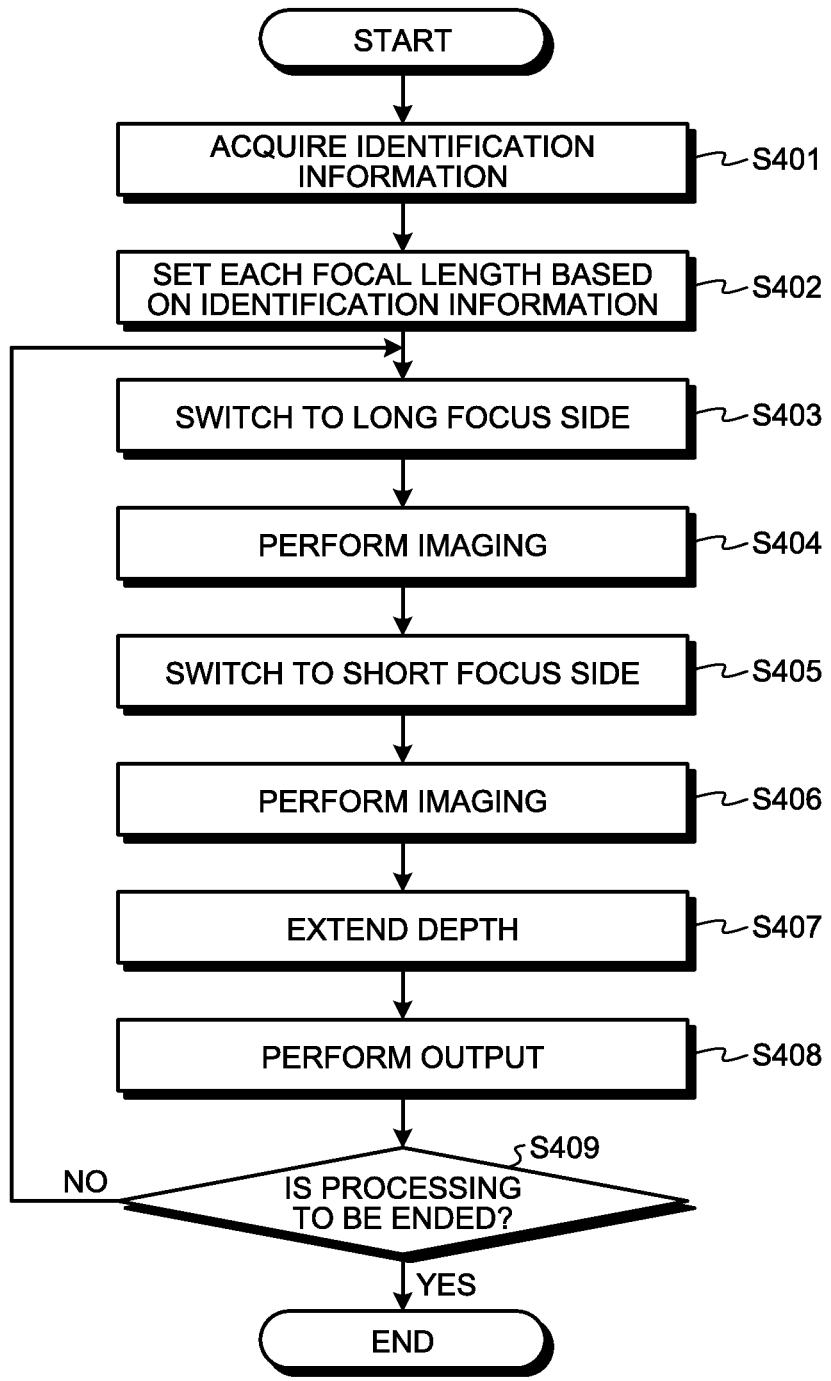
FIG. 14 is a flowchart illustrating an outline of processing executed by the endoscope system according to the fifth embodiment.

FIG. 14 is a flowchart illustrating the outline of the processing executed by the endoscope system 1B.

As illustrated in FIG. 14, the identification information acquirer 95 first acquires the identification information from the identification information recorder 201 of the insertion unit 2B, through the endoscope imaging device 5 and the first transmission cable 6 (Step S401).

Subsequently, the focal length setting unit 944 sets each of the focal lengths on the long focus side and the short focus side of the electric lens 511 based on the identification information acquired by the identification information acquirer 95 (Step S402).

Steps S403 to S409 respectively correspond to Steps S201 to S207 described above. After Step S409, the endoscope system 1B ends this processing.

According to the fifth embodiment described above, since the focal length setting unit 944 sets each of the focal lengths on the long focus side and the short focus side of the electric lens 511 according to the identification information on the insertion unit 2B connected to the endoscope imaging device 5, an image at an extended depth of focus may be obtained in a state suitable for the insertion unit 2B.

In the fifth embodiment, the focal length setting unit 944 sets each of the focal lengths on the long focus side and the short focus side of the electric lens 511 according to the identification information on the insertion unit 2B connected to the endoscope imaging device 5. However, for example, a plurality of focal lengths of the electric lens 511 may be set according to the identification information on the insertion unit 2B connected to the endoscope imaging device 5. By this setting, an image with a more extended depth of field may be obtained.

In the fifth embodiment, the focal length setting unit 944 sets each of the focal lengths on the long focus side and the short focus side of the electric lens 511 according to the identification information on the insertion unit 2B connected to the endoscope imaging device 5. However, the focal length setting unit 944 may, for example, determine the type of the insertion unit 2B based on the video signal generated by the video signal generator 91, and set each of the focal lengths on the long focus side and the short focus side of the electric lens 511 based on this determination result. In this case, the focal length setting unit 944 only needs to determine the type of the insertion unit 2B based on an image corresponding to the video signal generated by the video signal generator 91 and images (template images) for identifying a plurality of respective insertion units 2B recorded in advance in the recorder 93, and to set each of the focal lengths on the long focus side and the short focus side of the electric lens 511 based on this determination result. Naturally, the focal length setting unit 944 may determine the type of the insertion unit 2B using any one or more parameters among the mask, the magnification, and the white balance of the image corresponding to the video signal generated by the video signal generator 91 and parameters for identifying the respective insertion units 2B recorded in advance in the recorder 93, and set each of the focal lengths on the long focus side and the short focus side of the electric lens 511 based on this determination result.

Sixth Embodiment

The following describes a sixth embodiment. Although the endoscope system 1A according to the second embodiment described above performs the imaging using a simultaneous method, an endoscope system according to the present sixth embodiment performs the imaging using a frame sequential method. The following describes the configuration of the endoscope system according to the present sixth embodiment, and then describes processing executed by the endoscope system according to the present sixth embodiment. The same components as those of the endoscope system 1A according to the above-described second embodiment are assigned with the same reference numerals, and the description thereof will not be repeated.

Configuration of Endoscope System

Figure 15:
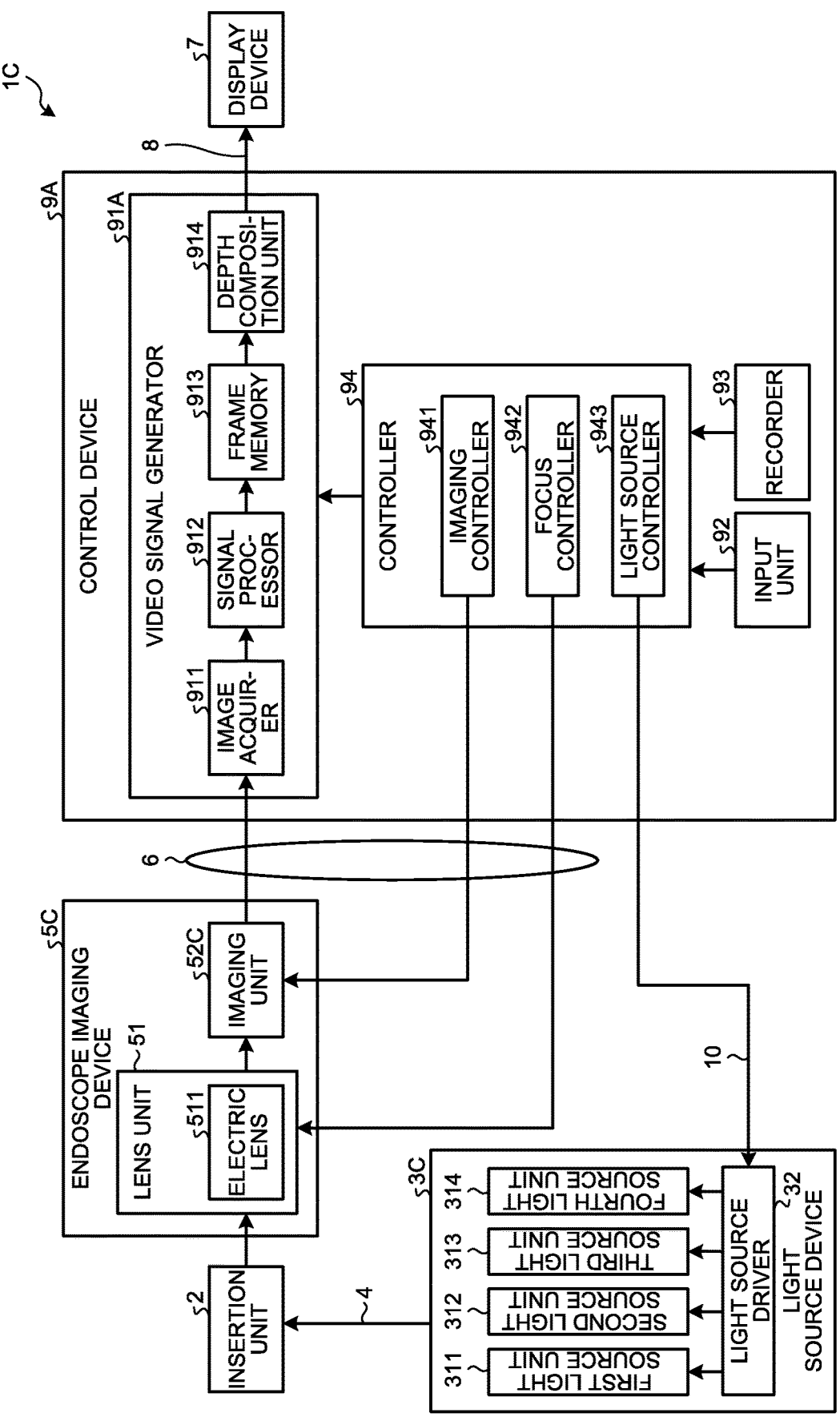
FIG. 15 is a block diagram illustrating functional configurations of an insertion unit, a light source device, an endoscope imaging device and a control device included in an endoscope system according to a sixth embodiment.

FIG. 15 is a block diagram illustrating functional configurations of an insertion unit, a light source device, an endoscope imaging device and a control device included in the endoscope system according to the sixth embodiment.

This endoscope system 1C illustrated in FIG. 15 includes a light source device 3C and an endoscope imaging device 5C instead of the light source device 3 and the endoscope imaging device 5 of the endoscope system 1A according to the second embodiment described above.

Configuration of Light Source Device

The configuration of the light source device 3C will first be described.

The light source device 3C periodically repeats emission of a plurality of illumination light beams having mutually different wavelength bands toward the insertion unit 2 at predetermined time intervals. As illustrated in FIG. 15, the light source device 3C includes a first light source unit 311, a second light source unit 312, a third light source unit 313, a fourth light source unit 314, and the light source driver 32.

The first light source unit 311 emits light having a blue wavelength band (450 nm to 495 nm) toward the insertion unit 2. The first light source unit 311 is configured using an LED lamp or the like.

The second light source unit 312 emits light having a green wavelength band (495 nm to 570 nm) toward the insertion unit 2. The second light source unit 312 is configured using an LED lamp or the like.

The third light source unit 313 emits light having a red wavelength band (620 nm to 759 nm) toward the insertion unit 2. The third light source unit 313 is configured using an LED lamp or the like.

The fourth light source unit 314 emits special light having predetermined wavelength bands (such as light including wavelength bands of 390 nm to 445 nm and 530 nm to 550 nm, or light including wavelength bands of 790 nm to 820 nm and 905 nm to 970 nm) toward the insertion unit 2. The fourth light source unit 314 is configured using an LED lamp or the like.

Configuration of Endoscope Imaging Device

The following describes the configuration of the endoscope imaging device 5C.

The eyepiece 21 of the insertion unit 2 (refer to FIG. 1) is detachably connected to the endoscope imaging device 5C. Under the control of the control device 9A, the endoscope imaging device 5C captures the observed image formed by the insertion unit 2, converts the captured image signal into the optical signal, and outputs the optical signal.

As illustrated in FIG. 15, the endoscope imaging device 5C includes the lens unit 51, and an imaging unit 52C.

The imaging unit 52C is configured using an image pickup device (not illustrated), such as a CCD or a CMOS, that receives the light of the subject image formed by the lens unit 51 and converts the received light into the electrical signal under the control of the control device 9A, and a sensor chip (not illustrated) provided by integrating, for example, a signal processor (not illustrated) that applies the signal processing (such as the analog-to-digital (A/D) conversion) to the electrical signal (analog signal) from the image pickup device to output the digital image signal. In the present sixth embodiment, the light receiving surface of the imaging unit 52C is provided with a monochromatic filter.

Processing by Endoscope System

Figure 16:
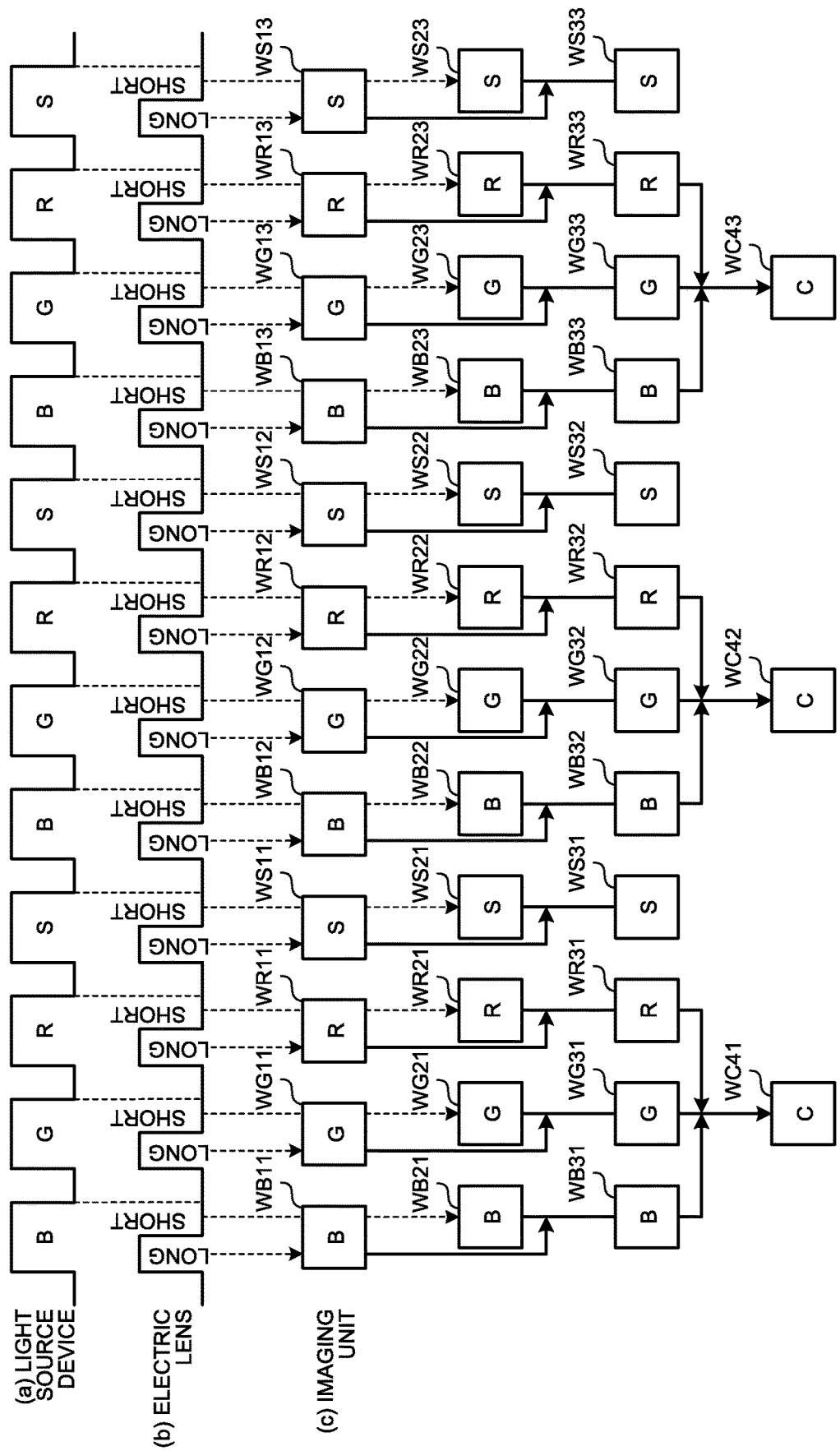
FIG. 16 illustrates a timing diagram of processing executed by the endoscope system according to the sixth embodiment.

The following describes processing executed by the endoscope system 1C. FIG. 16 illustrates a timing diagram of the processing executed by the endoscope system 1C. In FIG. 16, Part (a) of FIG. 16 illustrates the type of the illumination light emitted by the light source device 3C; Part (b) of FIG. 16 illustrates switching timing of the focal length of the lens unit 51; and Part (c) of FIG. 16 illustrates timing of image generation by the imaging unit 52C. For convenience of explanation, FIG. 16 expresses the light having the blue wavelength band, the light having the green wavelength band, the light having the red wavelength band, and the light having the wavelength bands of the special light as B, G, R, and S, respectively. The light source device 3C emits S in FIG. 16, but may emit only B, G, and R, or emit only S, according to an operation of the input unit 92. In addition, for convenience of explanation, FIG. 16 illustrates the switching of the focal length of the electric lens 511 between the two sides of the long focus side and the short focus side. The switching is, however, not limited thereto. The focus controller 942 may perform the control to, for example, repeat the sequential switching of the focal length of the electric lens 511 between a plurality of focal lengths set according to the operations of the input unit 92.

As illustrated in FIG. 16, the light source controller 943 controls the light source device 3C to emit the illumination light beams in the order of B, G, R, and S according to the predetermined timing. For example, by controlling the light source driver 32 of the light source device 3C based on the timing of 120 fps, the light source controller 943 drives the first light source unit 311, the second light source unit 312, the third light source unit 313, and the fourth light source unit 314, in this order, to emit B, G, R, and S. In this case, the focus controller 942 switches the focal length of the electric lens 511 between the long focus side and the short focus side within a time during which the light source device 3C emits one of the illumination light beams. For example, the focus controller 942 switches the focal length of the electric lens 511 between the long focus side and the short focus side at a timing of 240 fps. The imaging controller 941 controls the imaging unit 52C to perform the imaging based on the switching timing of the focal length of the electric lens 511. For example, the imaging controller 941 controls the imaging unit 52C to perform the imaging at the timing of 240 fps to generate an image synchronous with the switching timing of the focal length of the electric lens 511.

Specifically, as illustrated in FIG. 16, when the light source device 3C is emitting B, the imaging controller 941 controls the imaging unit 52C to perform the imaging when the focal length of the electric lens 511 is on the long focus side so as to generate a blue image WB11 in focus on the long focus side.

Thereafter, when the light source device 3C is emitting B, the imaging controller 941 controls the imaging unit 52C to perform the imaging when the focal length of the electric lens 511 is on the short focus side so as to generate a blue image WB21 in focus on the short focus side.

Then, the depth composition unit 914 uses the image WB11 and the image WB21 generated by the imaging unit 52C to generate a blue image WB31 with an extended depth of focus.

Subsequently, in the same manner as in the case of B, when the light source device 3C is emitting G, the imaging controller 941 controls the imaging unit 52C to perform the imaging when the focal length of the electric lens 511 is on the long focus side so as to generate a green image WG11 in focus on the long focus side.

Thereafter, when the light source device 3C is emitting G, the imaging controller 941 controls the imaging unit 52C to perform the imaging when the focal length of the electric lens 511 is on the short focus side so as to generate a green image WG21 in focus on the short focus side.

Then, the depth composition unit 914 uses the image WG11 and the image WG21 generated by the imaging unit 52C to generate a green image WG31 with an extended depth of focus.

Subsequently, in the same manner as in the cases of B and G, when the light source device 3C is emitting R, the imaging controller 941 controls the imaging unit 52C to perform the imaging when the focal length of the electric lens 511 is on the long focus side so as to generate a red image WR11 in focus on the long focus side.

Thereafter, when the light source device 3C is emitting R, the imaging controller 941 controls the imaging unit 52C to perform the imaging when the focal length of the electric lens 511 is on the short focus side so as to generate a red image WR21 in focus on the short focus side.

Then, the depth composition unit 914 uses the image WR11 and the image WR21 generated by the imaging unit 52C to generate a red image WR31 with an extended depth of focus.

Subsequently, the display device 7 displays one frame of color image WC41 based on the blue image WB31, the green image WG31, and the red image WR31. In this manner, the color image WC41 with an extended depth of field (color depth-of-field composite image) may be displayed.

In addition, in the same manner as in the cases of B, G, and R, when the light source device 3C is emitting S, the imaging controller 941 controls the imaging unit 52C to perform the imaging when the focal length of the electric lens 511 is on the long focus side so as to generate a special light image WS11 in focus on the long focus side.

Thereafter, when the light source device 3C is emitting S, the imaging controller 941 controls the imaging unit 52C to perform the imaging when the focal length of the electric lens 511 is on the short focus side so as to generate a special light image WS21 in focus on the short focus side.

Then, the depth composition unit 914 uses the image WS11 and the image WS21 generated by the imaging unit 52C to generate a special light image WS31 (special light depth-of-field composite image) with an extended depth of field.

Subsequently, the display device 7 displays the image WS31. In this manner, the special light image WS31 with an extended depth of focus may be displayed. Although the image WS31 is displayed after the color image WC41 in FIG. 16, the present disclosure is not limited thereto. The image WS31 may be excluded from being displayed.

As described above, in the endoscope system 1C, the light source controller 943 controls the light source device 3C to emit the illumination light beams in the order of B, G, R, and S according to the predetermined timing; the focus controller 942 switches the focal length of the electric lens 511 between the long focus side and the short focus side within the time during which the light source device 3C emits one of the illumination light beams; the imaging controller 941 controls the imaging unit 52C to sequentially perform the imaging based on the switching timing of the focal length of the electric lens 511; and the depth composition unit 914 generates the image with the extended depth of focus using two or more images of each color generated by the imaging unit 52C at different focal lengths. Then, the display device 7 combines the blue, green, and red images generated by the depth composition unit 914, and sequentially displays the color image WC41, a color image WC42, and a color image WC43 for each frame.

According to the sixth embodiment described above, the depth of field may be extended without an increase in size even in the case of the frame sequential method.

In the sixth embodiment, the depth composition unit 914 generates the image with the extended depth of field using temporally successive images. The present disclosure is, however, not limited thereto. The image with the extended depth of focus may be generated using temporally earlier and later images. Specifically, as illustrated in FIG. 16, the depth composition unit 914 may generate a blue image with an extended depth of field using images WB11 and WB22 recorded in the frame memory 913.

In the sixth embodiment, the depth composition unit 914 may generate the depth-of-field composite image with the extended depth of field using any of a plurality of images within a predetermined time recorded in the frame memory 913. Specifically, the depth composition unit 914 may generate a blue image with an extended depth of field using any one of images WB11, WB12, and WB13 on the long focus side and any one of images WB21, WB22, and WB23 serving as short focus images illustrated in FIG. 16. In the same manner, the depth composition unit 914 may generate a green image with an extended depth of field using any one of images WG11, WG12, and WG13 on the long focus side and any one of images WG21, WG22, and WG23 serving as short focus images illustrated in FIG. 16. Naturally, the depth composition unit 914 may generate a red image with an extended depth of field using any one of images WR11, WR12, and WR13 on the long focus side and any one of images WR21, WR22, and WR23 serving as short focus images. In the same manner, the depth composition unit 914 may generate a special light image with an extended depth of field using any one of images WS11, WS12, and WS13 on the long focus side and any one of images WS21, WS22, and WS23 serving as short focus images.

Figure 17:
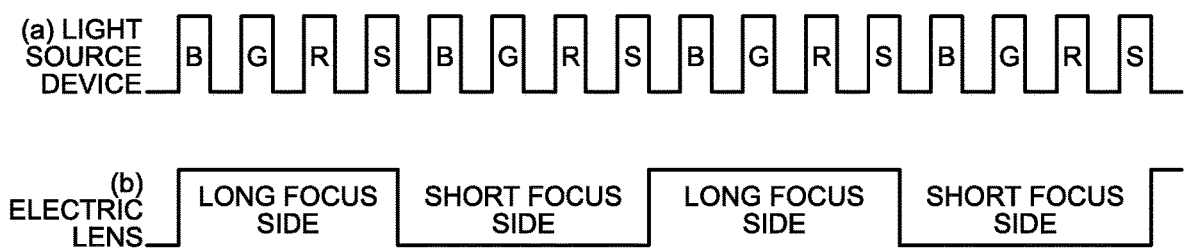
FIG. 17 illustrates a timing diagram of other processing executed by the endoscope system according to the sixth embodiment.

In the sixth embodiment, the focus controller 942 switches the focal length of the electric lens 511 between the long focus side and the short focus side within the time during which the light source device 3C emits one of the illumination light beams. The present disclosure is, however, not limited thereto. The focal length of the electric lens 511 may be switched, for example, after the light source device 3C has emitted B, G, R, and S. Specifically, as illustrated in FIG. 17, the focus controller 942 may sequentially switch the focal length of the electric lens 511 each time the light source device 3C has emitted one cycle of B, G, R, and S.

Seventh Embodiment

The following describes a seventh embodiment. In the second embodiment described above, the present disclosure is applied to the endoscope system using the rigid endoscope (insertion unit 2). In the seventh embodiment, however, the present disclosure is applied to an endoscope system using a flexible endoscope, that is, what is called a videoscope having a device for endoscope on the distal end side of the insertion unit. The same components as those of the endoscope system 1A according to the above-described second embodiment are assigned with the same reference numerals, and the description thereof will not be repeated.

Configuration of Endoscope System

Figure 18:
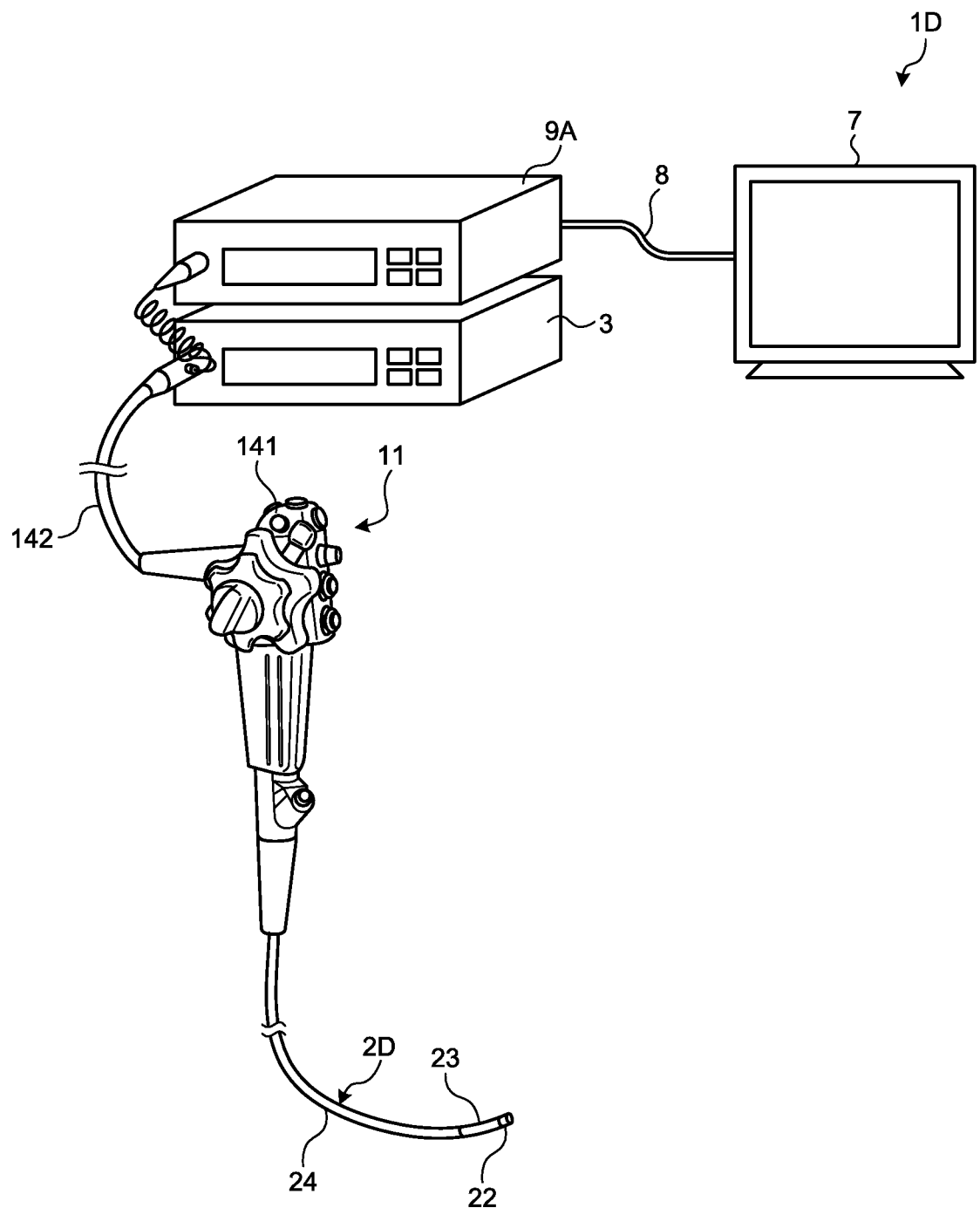
FIG. 18 is a diagram illustrating a schematic configuration of an endoscope system according to a seventh embodiment.

FIG. 18 is a diagram illustrating the schematic configuration of the endoscope system according to the seventh embodiment.

This endoscope system 1D illustrated in FIG. 18 includes an endoscope 11 for capturing an in vivo image of an observed part of the subject and outputting an image signal by inserting an insertion unit 2D into the living body, the light source device 3 for generating illumination light to be emitted from the distal end of the endoscope 11, the control device 9A for processing the image signal output from the endoscope 11 to generate and output a video signal, and the display device 7 for displaying an image based on the video signal.

As illustrated in FIG. 18, the endoscope 11 includes the insertion unit 2D that is flexible and has a long, thin shape, an operation unit 141 that is connected to the proximal end side of the insertion unit 2D and receives input of various operation signals, and a universal cord 142 that extends from the operation unit 141 in a direction different from the extending direction of the insertion unit 2D and is connected to the light source device 3 and the control device 9A, and that incorporates various cables including the first transmission cable 6.

As illustrated in FIG. 18, the insertion unit 2D includes a distal end portion 22 incorporating the above-described lens unit 51 (not illustrated) and the imaging unit 52 (not illustrated), a bendable bending portion 23 that is connected to the proximal end side of the distal end portion 22 and is composed of a plurality of bending pieces, and an elongated flexible tube portion 24 that is connected to the proximal end side of the bending portion 23 and has flexibility. The distal end portion 22 is provided with the imaging unit 52. The image signal obtained by the imaging by this imaging unit 52 is output to the control device 9A through the operation unit 141 and the universal cord 142 incorporating the first transmission cable 6. In this case, the number of effective pixels of the imaging unit 52 (image pickup device) is equal to or more than two megapixels (such as what is called the 2K resolution of 1920×1080 pixels).

The above-described seventh embodiment provides the same effect as that of the second embodiment described above even in the case where the flexible endoscope (endoscope 11) is used.

The seventh embodiment has been described by exemplifying the endoscope 11 in which the imaging unit 52 is provided at the distal end portion 22 of the flexible insertion unit 2D. The present disclosure may, however, be applied to the rigid endoscope in which the imaging unit is provided at the rigid insertion unit. In this case, the number of effective pixels of the imaging unit is preferably equal to or more than two megapixels (such as what is called the 2K resolution of 1920×1080 pixels) in the same manner as in the case of the imaging unit 52 of the seventh embodiment described above.

Other Embodiments

Figure 19A:
FIG. 19A is a diagram illustrating an exemplary image captured by an imaging unit according to another embodiment.
Figure 19B:
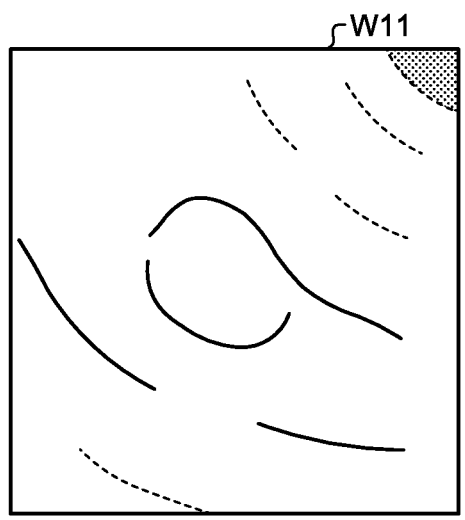
FIG. 19B is a diagram illustrating another exemplary image captured by the imaging unit according to the other embodiment.
Figure 19C:
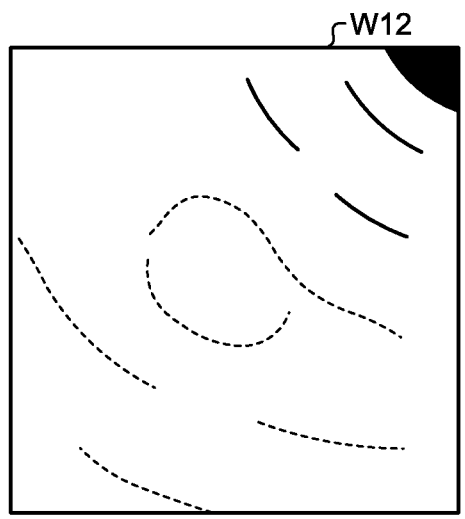
FIG. 19C is a diagram illustrating still another exemplary image captured by the imaging unit according to the other embodiment.
Figure 19D:
FIG. 19D is a diagram illustrating an exemplary image generated by the depth composition unit according to the other embodiment.

In the first to seventh embodiments described above, the focus controller 942 alternately switches the focal length of the electric lens 511 between the long focus side and the short focus side. The switching is, however, not limited thereto. The electric lens 511 may be switched between a plurality of focal lengths. For example, the focus controller 942 may sequentially switch the electric lens 511 between three focal lengths. In this case, as illustrated in FIGS. 19A to 19C, the imaging controller 941 controls the imaging unit 52 to generate an image W10, an image W11, and an image W12 corresponding to the respective focal lengths, according to the switching timing of the focal length of the electric lens 511. Then, as illustrated in FIG. 19D, the depth composition unit 914 uses the images W10, W11, and W12 generated by the imaging unit 52 to generate a composite image W13 (depth-of-field composite image) with an extended depth of field. In this manner, the image (depth-of-field composite image) with the more extended depth of field may be obtained.

In the description of the processing by the endoscope system described herein, the temporal relations between the respective steps have been indicated using expressions, such as "first", "thereafter", "subsequently", and "then". However, the order of the steps necessary for carrying out the present disclosure is not uniquely determined by those expressions. That is, the order of the processing by the endoscope system described herein may be changed as long as no inconsistency occurs.

Thus, the present disclosure may include various embodiments not described herein, and various design modifications and the like may be made within the scope of the technical ideas specified by claims.

The present disclosure provides an effect that the depth of field may be extended without an increase in device size.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An endoscope system comprising:
an electric lens capable of changing a focal length by applying a voltage;
a camera configured to capture a subject image formed by the electric lens to generate image signals; and
circuitry configured to:
alternately switch the focal length of the electric lens between a long focus side and a short focus side the focal length of which is smaller than that of the long focus side;
generate a video signal to be provided to a display from the image signals generated by the camera; and
control the camera such that an exposure time of the camera on the long focus side is longer than the exposure time of the camera on the short focus side.

2. The endoscope system according to claim 1, wherein the circuitry is configured to sequentially switch the focal length for each frame of the video signal.

3. The endoscope system according to claim 1, wherein the circuitry is configured to perform the control to switch the focal length during an output period in which the camera outputs the image signals.

4. The endoscope system according to claim 1, wherein the circuitry is further configured to generate the video signal with an extended depth of field using two or more of the image signals generated by the camera at different focal lengths.

5. The endoscope system according to claim 4, wherein circuitry is further configured to:
record the image signals of a plurality of frames for each of the focal lengths, and
generate the video signal with the extended depth of field using any one of the image signals of the frames recorded.

6. The endoscope system according to claim 1, further comprising:
a light source configured to emit illumination light having a predetermined wavelength band, wherein the circuitry is
configured to:
alternately switch the focal length of the electric lens between a lone focus side and a short focus side the focal length of which is smaller than that of the lone focus side; and
control the light source such that an intensity of the illumination light on the long focus side is higher than the intensity of the illumination light on the short focus side.

7. The endoscope system according to claim 1, wherein the circuitry is further configured to:
receive an instruction signal indicating any one of a depth extension mode in which the focal length of the electric lens is alternately switched between the long focus side and the short focus side, a search mode in which the focal length of the electric lens is fixed to the long focus side, and a treatment mode in which the focal length of the electric lens is fixed to the short focus side, and
control the focal length of the electric lens according to the instruction signal.

8. The endoscope system according to claim 1, further comprising:
scope that is insertable into a subject and includes a plurality of optical members, wherein the circuitry is further configured to:
acquire identification information identifying a type of the scope;
set a plurality of focal lengths of the electric lens based on the identification information; and
periodically repeat sequential switching of the focal length of the electric lens between the focal lengths.

9. The endoscope system according to claim 1, further comprising a light source to periodically repeat emission of a plurality of illumination light beams having mutually different wavelength bands, wherein
the circuitry is configured to alternately switch the focal length of the electric lens between the long focus side and the short focus side during an emission period in which the light source emits one of the illumination light beams.

10. The endoscope system according to claim 1, wherein the electric lens is a liquid lens.

11. The endoscope system according to claim 1, further comprising:
a scope insertable into a subject; and
an endoscope imager to be detachably connected to the scope, wherein
the endoscope imager includes the camera, and
number of effective pixels of the camera is equal to or more than eight mega pixels.

12. The endoscope system according to claim 1, further comprising a scope insertable into a subject, wherein
the scope includes the camera at a distal end thereof, and
number of effective pixels of the camera is equal to or more than two mega pixels.

13. The endoscope system according to claim 1, further comprising a display to display an image corresponding to the video signal, wherein the display has a monitor size of 31 inches or larger.

14. An endoscope system, comprising:
    an electric lens capable of changing a focal length by applying a voltage;
    a camera configured to capture a subject image formed by the electric lens to generate image signals;
    a light source configured to emit illumination light having a predetermined wavelength band; and
    circuitry configured to:
    alternately switch the focal length of the electric lens between a long focus side and a short focus side the focal length of which is smaller than that of the long focus side;
    generate a video signal to be provided to a display from the image signals generated by the camera; and
    control the light source such that an intensity of the illumination light on the long focus side is higher than the intensity of the illumination light on the short focus side.

15. An endoscope system, comprising:
    an electric lens capable of changing a focal length by applying a voltage;
    a camera configured to capture a subject image formed by the electric lens to generate image signals;
    a scope that is insertable into a subject and includes a plurality of optical member; and
    circuitry configured to:
        generate a video signal to be provided to a display from the image signals generated by the camera;
        acquire identification information identifying a type of the scope;
        set a plurality of focal lengths of the electric lens based on the identification information; and
        periodically repeat sequential switching of the focal length of the electric lens between the plurality of focal lengths.

16. The endoscope system according to claim 15, wherein the circuitry is configured to alternately switch the focal length of the electric lens between a long focus side and a short focus side the focal length of which is smaller than that of the long focus side.

17. The endoscope system according to claim 16, wherein the circuitry is further configured to control the camera such that an exposure time of the camera on the long focus side is longer than the exposure time of the camera on the short focus side.

18. An endoscope system comprising:
    an electric lens capable of changing a focal length by applying a voltage;
    a camera configured to capture a subject image formed by the electric lens to generate image signals;
    a light source to periodically repeat emission of a plurality of illumination light beams having mutually different wavelength bands; and
    circuitry configured to:
    alternately switch the focal length of the electric lens between a long focus side and a short focus side the focal length of which is smaller than that of the long focus side;
    generate a video signal to be provided to a display from the image signals generated by the camera; and
    alternately switch the focal length of the electric lens between the long focus side and the short focus side during an emission period in which the light source emits one of the illumination light beams.

* * * * *